US009176105B2

(12) United States Patent
Mace et al.

(10) Patent No.: US 9,176,105 B2
(45) Date of Patent: Nov. 3, 2015

(54) DENSITY-BASED SEPARATION OF BIOLOGICAL ANALYTES USING MULTIPHASE SYSTEMS

(75) Inventors: Charles R. Mace, Auburn, NY (US); Ashok A. Kumar, Cambridge, MA (US); Dyann F. Wirth, Boston, MA (US); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/817,985

(22) PCT Filed: Aug. 22, 2011

(86) PCT No.: PCT/US2011/048678
§ 371 (c)(1),
(2), (4) Date: Jul. 1, 2013

(87) PCT Pub. No.: WO2012/024693
PCT Pub. Date: Feb. 23, 2012

(65) Prior Publication Data
US 2013/0280693 A1    Oct. 24, 2013

Related U.S. Application Data

(60) Provisional application No. 61/375,532, filed on Aug. 20, 2010.

(51) Int. Cl.
*A01N 1/02*   (2006.01)
*G01N 33/18*   (2006.01)
*B03B 5/28*   (2006.01)
*B03B 5/44*   (2006.01)
*B03D 3/00*   (2006.01)
*G01N 33/49*   (2006.01)
*G01N 33/537*   (2006.01)
*G01N 33/574*   (2006.01)

(52) U.S. Cl.
CPC *G01N 33/18* (2013.01); *B03B 5/28* (2013.01); *B03B 5/442* (2013.01); *B03D 3/00* (2013.01); *G01N 33/491* (2013.01); *G01N 33/5375* (2013.01); *G01N 33/57492* (2013.01)

(58) Field of Classification Search
USPC .................................................. 435/2, 34
See application file for complete search history.

(56) References Cited

U.S. PATENT DOCUMENTS

| 2,825,698 | A |   | 3/1958 | Taylor et al. |
| 4,740,304 | A |   | 4/1988 | Tjerneld et al. |
| 5,316,540 | A |   | 5/1994 | McMannis et al. |
| 5,432,054 | A |   | 7/1995 | Saunders et al. |
| 5,772,888 | A |   | 6/1998 | Liu et al. |
| 5,840,502 | A | * | 11/1998 | Van Vlasselaer ............ 435/7.21 |
| 5,962,237 | A |   | 10/1999 | Ts'o et al. |
| 6,048,715 | A |   | 4/2000 | Haynes et al. |
| 6,210,889 | B1 |   | 4/2001 | Drouin et al. |
| 6,454,950 | B1 |   | 9/2002 | Tjerneld et al. |
| 6,677,439 | B1 |   | 1/2004 | Blanco et al. |
| 2007/0036722 | A1 |   | 2/2007 | Rongved et al. |
| 2007/0067463 | A1 |   | 3/2007 | Ishibashi et al. |
| 2007/0125716 | A1 |   | 6/2007 | Procter et al. |
| 2007/0249502 | A1 |   | 10/2007 | Procter et al. |
| 2009/0325218 | A1 |   | 12/2009 | Melis |
| 2010/0041014 | A1 | * | 2/2010 | Hyde et al. ........................ 435/5 |
| 2010/0120085 | A1 | * | 5/2010 | Hyman et al. .................. 435/34 |
| 2010/0129857 | A1 |   | 5/2010 | Walsh et al. |
| 2013/0280693 | A1 |   | 10/2013 | Mace et al. |
| 2013/0313483 | A1 | * | 11/2013 | Mace et al. ................ 252/408.1 |

FOREIGN PATENT DOCUMENTS

| CA | 2358326 | 4/2003 |
| EP | 0954524 B1 | 4/2003 |
| EP | 1159290 | 5/2004 |
| GB | 2239197 | 6/1991 |
| IL | 106488 | 8/1996 |
| JP | 5229951 | 9/1993 |
| WO | WO-87/05393 | 9/1987 |
| WO | WO-91/04318 A1 | 4/1991 |
| WO | WO 96/04556 * | 2/1996 |
| WO | WO-2004/018066 A2 | 3/2004 |
| WO | WO-2006/003134 A1 | 1/2006 |
| WO | WO-2007/067463 A1 | 6/2007 |
| WO | WO-2007/067728 A1 | 6/2007 |
| WO | WO-2008/049083 A2 | 4/2008 |
| WO | WO-2008/156409 A1 | 12/2008 |
| WO | WO-2008/156410 A1 | 12/2008 |
| WO | WO-2012/024688 | 2/2012 |
| WO | WO-2012/024690 A1 | 2/2012 |
| WO | WO-2012/024691 A1 | 2/2012 |
| WO | WO-2012/024693 A1 | 2/2012 |

OTHER PUBLICATIONS

Albertsson, Per-ake et al. "Affinity Separation of Proteins in Aqueous Three-Phase Systems." Analytical Biochemistry. vol. 175, No Month Listed 1988. pp. 154-161. 8 pages.

(Continued)

*Primary Examiner* — Ralph Gitomer
(74) *Attorney, Agent, or Firm* — Wilmer Cutler Pickering Hale and Dorr LLP

(57) ABSTRACT

The disclosed methods use a multi-phase system to separate samples according to the density of an analyte of interest. The method uses a multi-phase system that comprises two or more phase-separated solutions and a phase component such as a surfactant or polymer. The density of the analyte of interest differs from the densities of the rest of the sample. The density of the analyte of interest is substantially the same as one or more phases. Thus, when the sample is introduced to the multi-phase system, the analyte of interest migrates to the phase having the same density as the analyte of interest, passing through one or more phases sequentially.

31 Claims, 12 Drawing Sheets

(56) References Cited

OTHER PUBLICATIONS

Albertsson, Per-Ake. "Application of the Phase Partition Method to a Hydrophobic Membrane Protein, Phospholipase A1 from *Escherichia coli*." Biochemistry. vol. 12, No. 13, No Month Listed 1973. pp. 2525-2530. 6 pages.

Asenjo, J.A. et al. "Phase Separation Rates of Aqueous Two-Phase Systems: Correlation with System Properties." Biotechnology and Bioengineering, vol. 79, No. 2, Jul. 20, 2002. pp. 217-223. 7 pages.

Grover, William H. et al. "Measuring Single-Cell Density." PNAS. vol. 108, No. 27, Jul. 5, 2011. pp. 10992-10996, 5 pages.

International Search Report and Written Opinion for International Application No. PCT/US2011/048673 mailed Jan. 20, 2012. 20 pages.

International Search Report and Written Opinion for International Application No. PCT/US2011/048675 mailed Nov. 2, 2011. 9 pages.

International Search Report and Written Opinion for International Application No. PCT/US2011/048676 mailed Nov. 2, 2011. 9 pages.

International Search Report and Written Opinion for International Application No. PCT/US2011/048678 mailed Nov. 2, 2011. 10 pages.

Ruan, Ke et al. "Interfacial Tension of Aqueous Three-Phase Systems Formed by Triton X-100/PEG/Dextran." Journal of Dispersion Science and Technology, 27, No Month Listed 2006. pp. 927-930. 5 pages.

Wong et al., "Egg Beater as Centrifuge: Isolating Human Blood Plasma from Whole Blood in Resource-poor Setting," Lab Chip, published online Oct. 14, 2008, 8, pp. 2032-2037, 6 pages.

Chiu, Thomas T. et al. "Poly(2-ethyl-2-oxazoline): A New Water- and Organic-Soluble Adhesive." Advances in Chemistry. American Chemical Society, Washington, DC. vol. 213, Chapter 23, No Month Listed 1986. pp. 425-433. 9 pages.

Sivars, Ulf et al. "Mechanisms of Phase Behaviour and Protein Partitioning in Detergent/Polymer Aqueous Two-phase Systems for Purification of Integral Membrane Proteins." Biochimica et Biophysica Acta 1474. Elsevier Science B.V. No Month Listed 2000. pp. 133-146. 14 pages.

Lu, T. and Shan, G., "Mechanism of the Droplet Formation and Stabilization in the Aqueous Two-Phase Polymerization of Acrylamide," Journal of Applied Polymer Science, vol. 112, pp. 2859-2867 (Feb. 24, 2009).

\* cited by examiner

Whole Blood

E. coli doped Whole Blood

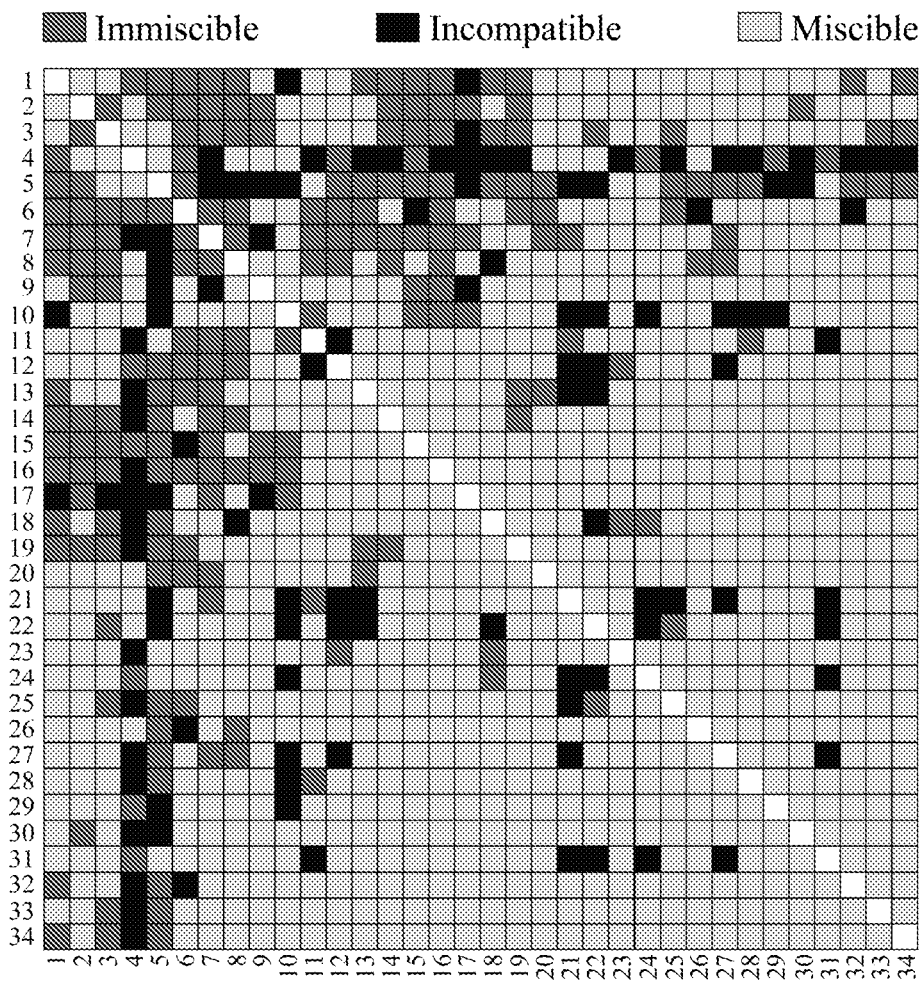

polymers and surfactants 1 polyacrylamide
2 Ficoll
3 dextran
4 poly(acrylic acid)
5 poly(methacrylic acid)
6 poly(ethylene glycol)
7 poly(2-ethyl-2-oxazoline)
8 poly(vinyl alcohol)
9 hydroxyethyl cellulose
10 polyallylamine
11 dextran sulfate
12 poly(diallyldimethyl ammonium chloride)
13 polyethyleneimine
14 Pluronic F68
15 Triton X-100
16 Tween 20
17 Brij 35
18 poly(propylene glycol)
19 3-[(3-cholamidopropyl)dimethylammonio]
    -1-propanesulfonate
20 1-$O$-octyl-β-D-glucopyranoside
21 poly(styrene sulfonic acid)
22 poly(2-acrylamido-2-methyl-
    1-propanesulfonic acid)
23 (hydroxypropyl)methyl cellulose
24 alginic acid
25 polyvinylpyrrolidone
26 carboxy-polyacrylamide
27 chondroitin sulfate A
28 sodium chloate
29 sodium dodecylsulfate
30 methyl cellulose
31 diethylaminoethyl-dextran
32 $N,N$-dimethyldodecylamine $N$-oxide
33 nonylphenol polyoxyethylene 20
34 Zonyl ial Patent
DENSITY-BASED SEPARATION OF BIOLOGICAL ANALYTES USING MULTIPHASE SYSTEMS

RELATED APPLICATIONS

This application is a National Stage Filing of PCT International Application No. PCT/US2011/048678, filed on Aug. 22, 2011, which claims priority to U.S. Provisional Patent Application No. 61/375,532, filed on Aug. 20, 2010, both of which are hereby incorporated by reference in their entirety. This application is also related to the following applications, the entire contents of which are incorporated herein by reference:

PCT Patent Application No. PCT/US2011/048673, filed on Aug. 22, 2011, entitled "MULTIPHASE SYSTEMS AND USES THEREOF";

PCT Patent Application No. PCT/US2011/048675, filed on Aug. 22, 2011, entitled "MULTIPHASE SYSTEMS HAVING MULTIPLE PHASE PROPERTIES"; and PCT Patent Application No. PCT/US2011/048676, filed on Aug. 22, 2011, entitled "MULTIPHASE SYSTEMS FOR ANALYSIS OF SOLID MATERIALS".

INCORPORATION BY REFERENCE

All non-patent literature, patents, patent applications and publications cited herein are hereby incorporated by reference in their entirety in order to more fully describe the state of the art as known to those skilled therein as of the date of the invention described herein.

BACKGROUND

It is known that the aqueous mixtures of two polymers such as poly(ethylene glycol) (PEG) and dextran can separate spontaneously into two aqueous phases, called aqueous two-phase systems. Phase separation in aqueous solutions of polymers is an extraordinary and underexplored phenomenon. When two aqueous solutions of polymers are mixed, the resulting system is not homogeneous; rather, two discrete phases, or layers, form. These layers are ordered according to density and arise from the limited interaction of the polymers for one another. In these systems, each phase predominantly consists of water (upwards of 70-90% (w/v)), while the polymer component is present in concentrations ranging from micromolar to millimolar. A low interfacial tension and rapid mass transfer of water-soluble molecules across the boundary characterize the interface between layers.

Previous studies of partitioning between aqueous phases have been limited to biphasic systems of immiscible polymers or inorganic salts. These Aqueous Two-Phase Systems ("ATPS") are exemplified by the poly(ethylene glycol)-dextran, dextran-Ficoll systems, and a poly(ethylene glycol) system comprising $(NH_4)_2SO_4$. Uses of these systems have focused on applications in protein chemistry, cell partitioning, and manufacturing.

Further, previous methods for separating and partitioning components have been limited to, e.g., filtration, crystallization, distillation, chromatography, and separation by hand. Many of these methods have been proven difficult, imprecise, slow, expensive, and unsuitable for use with diverse sample types and sizes, or otherwise undesirable.

There is a need for simple, precise methods for separating biological and non-biological samples based on density with multi-phase systems suitable for use with diverse sample types and sizes.

SUMMARY

Described herein are methods of separating or analyzing analytes of interest using multi-phase systems ("MPS") comprising two or more phases having different densities. In some embodiments, MPS as described herein are used to separate analytes from each other or from impurities and other objects in the sample when the analytes migrate to phases characteristic of their densities, and in so doing, contact each phase of the multi-phase system sequentially. In some embodiments, a multi-phase system comprising a phase component is used and the analyte contacts each phase of the multi-phase system sequentially. As used herein, "sequential contact" means that the analyte contacts and interacts with only one phase (and its phase component) at a time except at the interface where the analyte may contact and interact with two adjacent phases simultaneously. That is, the interaction of the analyte with the MPS occurs when the MPS has already phase separated and not during the process of phase separation.

The multi-phase systems used in the methods disclosed herein comprise two or more phases that are phase-separated from each other, wherein each of the two or more phases comprises a phase component. The phase component is one or more selected from the group consisting of polymer, surfactant, or combinations thereof, wherein at least one of the phase components is a polymer. The phases in the multi-phase system can be aqueous or organic. In some embodiments, at least one phase of the multi-phase system is aqueous and at least one phase of the multi-phase system is organic.

The phase component is selected from the group consisting of a polymer, a surfactant and combinations thereof. The phase "combination" refers to the combination of a polymer and a surfactant, a combination of two or more polymers, a combination of two or more surfactants, or a combination of any number of polymers and any number of surfactants.

As used herein, MPS refers to a multi-phase system. When two or more solutions containing a phase component are mixed, the resulting system is not homogeneous; rather, two or more discrete phases, or layers, form. These layers are ordered according to density and arise from the exhibit limited interaction of the phase components with one another. The two or more phases or solutions, which exhibit limited interaction and form distinct phase boundaries between adjacent phases. Each phase can be aqueous or non-aqueous. The non-aqueous phase comprises an organic liquid or an organic solvent.

As used herein, AMPS refers to an aqueous multi-phase polymer system. ATPS refers to an aqueous two-phase polymer system.

As used herein, an aqueous multi-phase polymer system comprises two or more polymer aqueous solutions or phases, which are phase-separated and in which at least two aqueous solutions each comprises a polymer. In some embodiments, the aqueous multi-phase polymer system can be combined with one or more immiscible organic phases to form a multi-phase system.

As used herein, the use of the phrase "polymer" includes, but is not limited to, the homopolymer, copolymer, terpolymer, random copolymer, and block copolymer. Block copolymers include, but are not limited to, block, graft, dendrimer, and star polymers. As used herein, copolymer refers to a polymer derived from two monomeric species; similarly, a terpolymer refers to a polymer derived from three monomeric species. The polymer also includes various morphologies, including, but not limited to, linear polymer, branched polymer, random polymer, crosslinked polymer, and dendrimer systems. As an example, polyacrylamide polymer refers to any polymer including polyacrylamide, e.g., a homopolymer, copolymer, terpolymer, random copolymer, block copolymer or terpolymer of polyacrylamide. Polyacrylamide can be a linear polymer, branched polymer, random polymer, crosslinked polymer, or a dendrimer of polyacrylamide.

In one embodiment, the a method of analyzing or separating a sample includes one or more biological analytes of interest using a multi-phase system, comprising: a) providing a multi-phase system comprising two or more phase-separated solutions, wherein each phase comprises a phase component selected from the group consisting of a polymer, a surfactant and combinations thereof, wherein at least one phase comprises a polymer; each said phase has an upper and a lower phase boundary; and each of the two or more phases has a different density and the phases, taken together, represent a density gradient; and b) introducing a biological sample comprising one or more biological analytes of interest without disrupting the phase-separated solution; and c) allowing each of the biological analytes to migrate to a location in the multi-phase system that is characteristic of its density, wherein during migration the sample contacts one or more of the two or more phases sequentially.

In another embodiment, a method of analyzing a sample comprising at least one analyte of interest according to the density of a tagged analyte of interest in a MPS is disclosed. The method comprises: a) providing a sample comprising at least one analyte of interest; b) combining the sample with a tag molecule to form a tag molecule-analyte adduct having a density different from the density of the analyte; c) providing a multi-phase system comprising two or more phases with clear boundaries, wherein at least one of the phases comprises a phase component, wherein the phase component is selected from the group consisting of a polymer, a surfactant, and combinations thereof; each of the two or more phases has a different density and the two or more phases, taken together, represent a density gradient; and the phases are phase-separated from each other; and d) introducing the sample comprising the tag molecule-analyte adduct to the multi-phase system; and e) allowing the tag molecule-analyte adduct to migrate to a location in the multiphase system that is characteristic of its density, wherein during migration the sample contacts one or more of the two or more phases sequentially and the analyte and the tag molecule-analyte adduct occupy different locations. As used herein, location means a position at, below, or above the interface between phases.

In still another embodiment, the method comprises: a) providing a sample comprising at least one analyte of interest; b) providing a multi-phase system comprising two or more phases with clear boundaries, wherein at least one of the phases comprises a phase component, wherein the phase component is selected from the group consisting of a polymer, a surfactant, and combinations thereof; each of the two or more phases has a different density and the two or more phases, taken together, represent a density gradient; and the phases are phase-separated from each other; c) introducing the sample comprising a tag molecule and the analyte to the multi-phase system, wherein the tag molecule and the analyte combine to form a tag molecule-analyte adduct having a density different from the density of the analyte; and d) allowing the tag molecule-analyte adduct to migrate to a location in the multiphase system that is characteristic of its density, wherein during migration the sample contacts one or more of the two or more phases sequentially and the analyte and the tag molecule-analyte adduct occupy different locations.

In another embodiment, a kit for separating a sample comprising one or more biological analytes of interest using a multi-phase system is disclosed. The kit comprises a) two or more phase components selected from the group consisting of a polymer, a surfactant, and combinations thereof; b) optionally a tag molecule capable of binding the one or more biological analytes of interest, wherein the tag molecule has a different density than the biological analyte of interest; and c) instructions for: (i) combining the two or more phase-separated solutions with a common solvent to create a multi-phase system; (ii) optionally, combining the biological analyte of interest and tag molecule, and (iii) separating the biological analyte of interest from the sample.

In one or more embodiments, the kit further comprising an aliquot of a common solvent which, when combined with the two or more phase components, provides a multiphase system.

In one aspect, the kit comprises instructions which direct that the biological analyte of interest be combined with the tag molecule to form a tag molecule-analyte adduct before introduction to the multi-phase system.

In another aspect, the kit comprises instructions that further direct that the biological analyte of interest and tag molecule be added to the multi-phase system to combine to form a tag molecule-analyte adduct in the multi-phase system.

In another aspect, the kit further comprises one or more additives selected from the group consisting of miscible surfactants, salts, dyes, nutrients, vitamins, antibiotics, anticoagulants, and buffers for combination with the phase components.

In some embodiments, the kit comprises a tag that has an affinity for one or more analytes of interest.

In one or more aspects, the tag has an affinity for one or more phase components.

In one or more aspects, the kit comprises a lytic agent for introduction into one or more phases of the multiphase system.

In one or more of the proceeding embodiments, the at least two phases share a common solvent.

In one or more of aspects, the multi-phase system is an aqueous system and the common solvent is an aqueous solvent.

In one or more of the preceding embodiments, the multi-phase system is a non-aqueous system and the common solvent is an organic solvent.

In one or more embodiment, the phase components are selected to be biologically compatible.

In one or more embodiments, the biological sample comprises cells. In one aspect, the cells are selected from the group consisting of animal, plant, protozoan, and prokaryotic cells.

In one or more embodiments, one or more phases comprise a lysing agent to cause the cells to lyse, the biological analyte of interest being recovered from cell lysate.

In one or more of the preceding embodiments, the biological analyte is selected from the group consisting of organelles, cell fragments, cell membranes, cell membrane fragments, viruses, virus-like particles, bacteriophage, cytosolic proteins, secreted proteins, signaling molecules, embedded proteins, nucleic acid/protein complexes, organelles, minicells, nucleic acid precipitants, chromosomes, nuclei, mitochondria, chloroplasts, flagella, biominerals, protein complexes, protein aggregates, and combinations thereof.

In one or more of the preceding embodiments, the biological sample comprises one or more parasites selected from the group consisting of worms, insects, protozoa, arachnids, and arthropods.

In one or more of the preceding embodiments, the biological sample comprises a biological fluid. In one or more aspects, the biological sample is selected from the group consisting of food, juice, and milk. In another aspect, the biological sample comprises one or biological carriers selected from the group consisting of whole blood, plasma, serum, sweat, feces, urine, saliva, tears, vaginal fluid, prostatic fluid, gingival fluid, amniotic fluid, intraocular fluid, cerebrospinal fluid, seminal fluid, sputum, ascites fluid, pus, nasopharengal fluid, wound exudate fluid, aqueous humour, vitreous humour, bile, cerumen, endolymph, perilymph, gastric juice, mucus, peritoneal fluid, pleural fluid, sebum, vomit, and combinations thereof.

In one or more aspects, the biological sample is tested for contaminants selected from the group consisting of pathogens, pests, heavy metals, and pesticides.

In the embodiments of the preceding claims, biological analyte is separated and analyzed to distinguish cell states selected from the group consisting of normal cells, diseased cells, parasitized cells, cancer cells, foreign cells, and infected cells.

In one or more embodiments, the sample comprises a plurality of analytes and each analyte migrates to a different location in the phase-separated system.

In one or more embodiments, after migration, the analyte resides at a boundary location.

In one or more of the preceding embodiments, the boundary location is at an interface between a phase with a density greater than the density of the analyte and a phase with a density that is less than the density of the analyte.

In one or more aspects, after migration, the analyte resides within a phase of the phase-separated system whose density matches the density of the analyte.

In another aspect, the analyte/phase-separated system is centrifuged to accelerate migration of the analyte.

In some aspects, the analyte migrates under gravitational forces. In other aspects, the analyte migrates under buoyancy forces.

In one or more of the preceding embodiments, the phase separated system is supported in a column or test tube.

In one or more of the preceding embodiments, the phase separated system is supported in a capillary tube, plastic test tube, falcon tube, culture tube, well plates, cuvette, along a filament, or on a sheet.

In one or more aspects, the sample comprises one or more biological analytes of interest. In other aspects, the sample comprises one or more non-biological analytes of interest.

In one or more aspects, the multi-phase system comprises one or more biologically compatible phases.

In one or more aspects, the surfactant is selected from the group consisting of polysorbate, 3-[(3-cholamidopropyl)dimethylammonio]-1-propanesulfonate ("CHAPS"), polyoxyethylene-polyoxypropylene, 1-O-Octyl-β-D-glucopyranoside, 4-(1,1,3,3-Tetramethylbutyl)phenyl-polyethylene glycol, 2-(Perfluoroalkyl)ethyl methacrylate, N,N-dimethyldodecylamine N-oxide, polyethylene glycol dodecyl ether, sodium dodecyl sulfate, sodium cholate, nonylphenol polyoxyethylene, benzylalkonium chloride, and dodecyltrimethylammonium chloride.

In one or more aspects of the preceding embodiment, the polymer is selected from the group consisting of dextran, polysucrose, poly(vinyl alcohol), poly(2-ethyl-2-oxazoline), poly(methacrylic acid), poly(ethylene glycol), polyacrylamide, polyethyleneimine, hydroxyethyl cellulose, polyvinylpyrrolidone, carboxy-polyacrylamide, poly(acrylic acid), poly(2-acrylamido-2-methyl-1-propanesulfonic acid), poly(diallyldimethyl ammonium chloride), poly(styrene sulfonic acid), polyallylamine, alginic acid, dextran sulfate, chondroitin sulfate A, diethylaminoethyl-dextran, poly(2-vinylpyridine-N-oxide), polydimethylsiloxane, and polypropylene glycol). In some aspects, the polymer is selected from the group of GRAS polymers. In one or more aspects, the polymer is selected from the group of homopolymers, random copolymers, block copolymers, graft copolymers, ter-polymers, dendrimers, star polymers and combinations thereof. In still other aspects, the polymer is linear, branched and/or cross-linked.

In one or more of the preceding embodiments, the method comprises a system further comprising one or more additives selected from the group consisting of miscible surfactants, salts, dyes, nutrients, vitamins, antibiotics, anticoagulants, and buffers.

In at least one aspect, the sample comprises the analyte of interest and one or more impurities, the impurity having the same density of the analyte, and the impurity having a different density than the tag molecule-analyte adduct.

In one or more aspects, the analyte of interest has an affinity for the tag molecule, and wherein the analyte of interest and tag molecule preferentially link to form a tag molecule-analyte adduct, the tag molecule-analyte adduct being linked by a method selected from the group consisting of covalent bonding, non-covalent bonding, hybridization, electrostatic interactions, complexation, and conjugation.

In one or more aspect, the tag in the tag molecule-analyte adduct has an affinity for one or more phase components, the tag of the tag molecule-analyte adduct and the phase component preferentially linking such that the tag molecule-analyte adduct preferentially aggregates in one or more phases containing phase components.

BRIEF DESCRIPTION OF THE DRAWINGS

The subject matter is described with reference to the following figures, which are presented for the purpose of illustration only and are not intended to be limiting of the invention.

FIG. 12 is a graph showing the outcome of unique two-component mixtures of twenty-three aqueous polymer solutions and eleven aqueous surfactant solutions mixtures: no phase separation (miscible; grey box), formation of a precipitate or a gel (incompatible; black box), and phase separation (immiscible; red box).

DETAILED DESCRIPTION

Introduction

Figure 1:
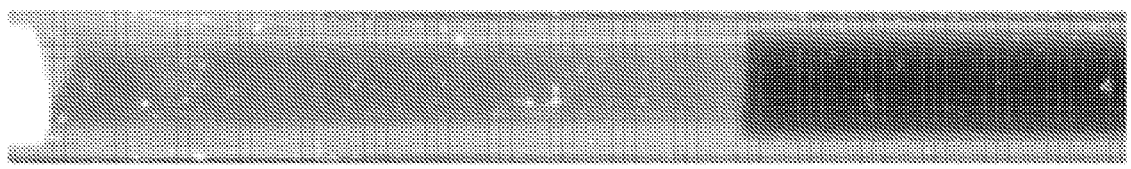
FIG. 1 shows separation of $E.\ coli$ from the cellular components of human whole blood using a PEG/Ficoll system with density steps at approximately 1.030 and 1.101 g/ml in which a strong increase in signal was seen when $E.\ coli$ was added to blood at a concentration of $10^6$ CFU/mL.
Figure 1:
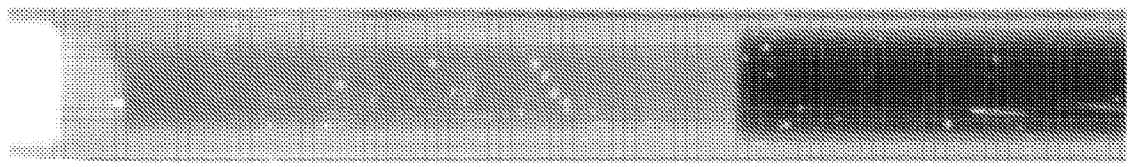

The disclosed methods are used to separate objects or impurities in samples according to the densities of the objects or impurities, relative to the densities of the phases of a MPS. Everything has a density. Thus, because the disclosed methods can be used to separate, isolate, characterize, analyze, prepare, and purify such diverse objects, the disclosed methods can be applied to many contexts. For example, the disclosed methods can be used in the forensics science context to separate and process objects of interest from complex samples, e.g., to separate mixtures of different types of biological samples (e.g., saliva or blood), or to separate biological samples from non-biological samples (e.g., separating bone from rock and other debris). These methods can be used to separate organisms from, or study organisms in seawater, irrigation water, or mine effluent. For example, the disclosed methods can be used with seawater to study small ocean organisms to keep buoyant densities close to what they are in nature, or with irrigation water or mine effluent to study the density effects on micro-organisms when exposed to these liquids. The disclosed methods can also be used monitor animal and plant health. Animal tissues and plant material can be broken down to the cellular level to detect cellular abnormalities indicative of disease and infection. The disclosed methods of separating and analyzing objects can also be used in pharmaceutical processing to detect and quantify impurities. Similarly, these methods can be used to detect contaminants such as pathogens, pests, heavy metals, and pesticides in food processing to ensure quality control.

Multi-Phase System

MPS for use in the separation of biological analytes are described. The multi-phase system comprises two or more phases which are phase-separated from each other, wherein each of the phases comprises a phase component. Each of the two or more phases has a different density and the phases, taken together, represent a density gradient, with the density of the phases increasing from the top phase to the bottom phase of the MPS as the MPS is viewed vertically. The phase component is a polymer, surfactant, or combinations thereof. The phases in the MPS can be aqueous or organic. In some embodiments, at least one phase of the MPS is aqueous and at least one phase of the MPS is organic. In some instances, such as when the sample contains biological analytes that must be kept active or living, it may be desirable for the MPS to comprise biologically compatible or substantially biologically compatible phases and phase components. For example, the solution can be an appropriately buffered aqueous solution and the phase components are selected for biocompatibility.

In some embodiments, the multi-phase polymer system comprises at least three phases. In some embodiments, the multi-phase system comprises at least four phases. In some embodiments, the multi-phase polymer system comprises at least five phases. In some embodiments, the multi-phase polymer system comprises at least six phases. Multi-phase systems with more phases are contemplated. The MPS includes at least two phases with a common solvent. However, when more than two phases are used, it is possible to include phases using different solvents. It is also possible to include phases that do not include a phase component, such as aqueous or organic solvents, liquid polymers, liquid metals, fluorinated liquids, and ionic liquids. Such variety improves the ability of the system to separate complex samples.

The MPS used in the disclosed methods can comprise aqueous phases, non-aqueous phases, or a combination of aqueous and non-aqueous phases. In some embodiments, each of the adjacent phases shares a common organic solvent. In some embodiments, each of the two or more phases is organic. In some embodiments, each of the two or more phases is aqueous. In some embodiments, the multi-phase system comprises at least one aqueous phase and at least one organic phase.

In some embodiments, the multi-phase system is aqueous and each phase of the MPS comprises a phase component soluble in the aqueous solvent. Non-limiting examples of aqueous solvent include water, $D_2O$, buffered water, e.g., phosphate buffers, cell lysis buffer, cell culture medium, e.g., nutrient media, selective media, transport media, enriched media, seawater, mine effluent, and irrigation water. In some embodiments, the aqueous MPS can comprise additional one or more organic phases comprising organic solvents. The organic phase exhibits limited interaction with, and phase-separated from, the aqueous polymer phases, however the phase component including the organic phase is soluble in an organic solvent.

In some specific embodiments, the multi-phase system further comprises one or more additional phases selected from the group consisting of organic solvents, ionic liquids, silicone oils, organic oils, fluorinated liquids, and metals that are liquid at room temperature. Suitable organic liquids include those that exhibit limited interaction with water and will phase-separate from the aqueous phases. Such additional phases are not required to have a phase component.

In some embodiments, the multi-phase system is organic and each phase of the MPS comprises a phase component dissolved in an organic solvent. Non-limiting examples of organic solvent include chloroform, ether, ethyl acetate, per-fluorinated solvents, oils, dichloromethane, tetrahydrofuran, toluene, tetrabromoethane, methanol, dimethylsulfoxide, ethanol, supercritical $CO_2$, fuel, methanol, and lubricant. In some specific embodiments, the different phases of the MPS comprise the same organic solvent. In other specific embodiments, the different phases of the MPS comprise different organic solvent. In other embodiments, the MPS comprises a liquid polymer as one of the phases. Non-limiting examples of liquid polymers include polydimethylsiloxane, poly(propylene glycol), poly(ethyl vinyl ether), cis(polyisoprene), polyethyleneimine, polybutadiene, polydimethylsiloxane, poly(propylene glycol), poly(ethyl vinyl ether), cis(polyisoprene) and polysorbate (herein referred to by the trade name "Tween").

In some embodiments, the MPS comprises at least an aqueous phase and at least one organic phase. Each phase may comprise a phase component and the mixture of aqueous and organic phases, taken together, represent a density gradient.

One component of an MPS can be a polymer. Non-limiting examples of polymers include GRAS polymers, dextran, polysucrose (herein referred to by the trade name "Ficoll"), poly(vinyl alcohol), poly(2-ethyl-2-oxazoline), poly(methacrylic acid), poly(ethylene glycol), polyacrylamide, polyethyleneimine, hydroxyethyl cellulose, polyvinylpyrrolidone, carboxy-polyacrylamide, poly(acrylic acid), poly(2-acrylamido-2-methyl-1-propanesulfonic acid), poly(diallyldimethyl ammonium chloride), poly(styrene sulfonic acid), polyallylamine, alginic acid, poly(2-vinylpyridine-N-oxide), diethylaminoethyl dextran, dextran sulfate, chondroitin sulfate A, polydimethylsiloxane, and poly(propylene glycol). In one or more aspects the polymer is selected from the group consisting of wherein the surfactant is selected from the group consisting of dextran, polysucrose, poly(vinyl alcohol), poly(2-ethyl-2-oxazoline), poly(methacrylic acid), poly(ethylene glycol), polyacrylamide, polyethyleneimine, hydroxyethyl cellulose, polyvinylpyrrolidone, carboxy-polyacrylamide, poly(acrylic acid), poly(2-acrylamido-2-methyl-1-propanesulfonic acid), poly(diallyldimethyl ammonium chloride), poly(styrene sulfonic acid), polyallylamine, alginic acid, dextran sulfate, chondroitin sulfate A, diethylaminoethyl-dextran, poly(2-vinylpyridine-N-oxide), polydimethylsiloxane, and poly(propylene glycol). In some embodiments, the polymer is selected from the group consisting of homopolymer, block copolymer, random copolymer, copolymer, terpolymer, and combinations thereof. In some embodiments, the polymer has a morphology selected from a group consisting of linear polymer, branched polymer, co-polymer, cross linked polymer, and dendrimer system. In some embodiments, the MPS comprises a polymer soluble in the solvent. In other embodiments, the MPS comprises a polymer soluble in water.

One component of an MPS can be a surfactant. Non-limiting examples surfactants that can be used to modify surface tension include Tween, CHAPS, polyoxyethylene-polyoxypropylene (herein referred to by the trade name "Pluronic F68"), 1-O-Octyl-β-D-glucopyranoside, 4-(1,1,3,3-Tetramethylbutyl)phenyl-polyethylene glycol (herein referred to by the trade name "Triton"), 2-(Perfluoroalkyl)ethyl methacrylate (herein referred to by the trade name "Zonyl"), N,N-dimethyldodecylamine N-oxide, polyethylene glycol dodecyl ether (herein referred to by the trade name "Brij"), sodium dodecyl sulfate, nonylphenol polyoxyethylene, sodium cholate, benzylalkonium chloride, and dodecyltrimethylammonium chloride. In some specific embodiments, surfactant phases comprising Pluronic F68 and CHAPS are selected to form an aqueous multi-phase polymer system with one or more aqueous polymer phases. Non-limiting examples of the polymer used in these embodiments include poly(methacrylic acid), poly(2-ethyl-2-oxazoline), dextran, Ficoll, polyacrylamide, and polyethyleneimine. In one or more aspects, the surfactant is selected from the group consisting of Tween 20, CHAPS, Pluronic F68, 1-O-Octyl-β-D-glucopyranoside, Triton, Zonyl, N,N-dimethyldodecylamine N-oxide, Brij, sodium dodecyl sulfate, sodium cholate, nonylphenol polyoxyethylene, benzylalkonium chloride, and dodecyltrimethylammonium chloride. The use of the surfactant can provide additional aqueous phases and facilitate the formation of the MPS. Other appropriate surfactants to accomplish this objective can be selected by the persons of ordinary skills in the art.

The aqueous surfactant phase and the aqueous polymer phase exhibit limited interaction and thus phase-separate. In some embodiments, more than one additional aqueous surfactant phase can be added to the aqueous multi-phase polymer system. In some specific embodiments, two aqueous surfactant phases and one or more aqueous polymer phases phase-separate and form an aqueous multi-phase polymer system.

In some aspects, one or more of the phases of the MPS comprises light or heavy salts one or more salts that aid in the phase-separation process. The salts dissolve in the phase, resulting in a change of the phase density, ionic strength or solubility of the phase component in the phase solvent. Non-limiting examples of salt include sodium chloride, potassium chloride, sulfates, phosphates, nitrites, citrates, EDTA, heparin, acids (e.g., HCl), bases (e.g., NaOH), glycine, buffer salts (e.g., tris(hydroxymethyl)aminomethane), acetates, and sulfonates. In some embodiments, salt(s) can be added to the polymer systems in order to adjust the density, pH, and/or osmolality of the multiphase systems.

In some embodiments, small molecules can be added for some specific functions. For example, in some specific embodiments, heparin or sodium EDTA are added as an anti-coagulant. In some other embodiments, sodium benzoate is added as a preservative.

In one or more embodiments, particularly multi-phase systems designed for use with more than two phase components, one or more polymers or surfactants that do not phase separate with each of the other phase components can be used as additives to modify the density, viscosity, osmolality, or refractive index of the phase component in which the additive resides. The polymers or surfactants are added to the various phases of the multi-phase system in addition to the phase components at concentrations less than is required to phase separate into a separate phase. In this instance, the surfactant performs the functions that are typical of surfactants, such as modify the surface tension of the solution.

Non-limiting examples of other additives that can be included in the phases include used in formulations to produce aggregation include, organic additives such as dyes and reactive or non-reactive dissolved gasses and cosolvents. In addition, the additives can be colloids or micelles. The phase components are selected so that the resulting phases exhibit limited interaction and thus are phase-separated from each other. Phase-separation refers to the phenomena where two or more phases, each comprising a phase component, when mixed together, form the same number of distinct phases where each phase has clear boundaries and is separated from other phases. Each phase component used in the solution is selected to be soluble in the solvent of the phase, so that each phase is phase-separated from other adjacent phase(s). When the multi-phase polymer system is designed, each phase component is selected to predominantly reside in one particular phase of the multi-phase system. It should be noted that in the resulting multi-phase system, every phase could contain varying amounts of other phase components from other phases in the MPS, in addition to the selected desired phase component in that phase. Unless otherwise specified, the phase component composition in each phase of the multi-phase system recited herein generally refers to the starting phase component composition of each phase, or to the predominant phase component composition of each phase. In some embodiments, the phase component composition on a phase component comprises predominantly one phase component and small amount of one or more other phase components. In some embodiments, the phase component composition in a phase comprises about 70% of one phase component. In some embodiments, the phase component composition in a polymer phase comprises about 75% of one phase component. In some embodiments, the phase component composition in a phase comprises about 80% of one phase component. In some embodiments, the phase component composition on a phase comprises about 85% of one phase component by weight. In some embodiments, the phase component composition on a phase comprises about 90% of one phase component by weight. In some embodiments, the phase component composition in a phase comprises about 95% of one phase component. In some embodiments, the phase component composition in a phase comprises about 99% of one phase component by weight. Other combinations of phase component compositions are contemplated.

In some embodiments, the concentration of the phase component in the phase is from about 0.1% to about 50% (wt/vol). In some embodiments, the concentration of the phase component in the phase is from about 0.5% to about 40% (wt/vol). In some embodiments, the concentration of the phase component in the phase is from about 1% to about 20% (wt/vol). In some embodiments, the concentration of the phase component in the phase is from about 5% to about 10% (wt/vol). In some embodiments, the concentration of the phase component in the phase is about 10% (wt/vol). In some embodiments, the concentration of the phase component in the phase is about 15% (wt/vol). In some embodiments, the composition or density of the resulting phases in the multi-phase system could be affected by the starting concentration of the phase component phases.

In some embodiments, one or more of the phases of the MPS are degassed to remove residual amount of gas dissolved in the phases. In some embodiments, the phases are degassed to remove oxygen from the phase to avoid possible oxidation of the sample applied onto the MPS.

Various types of form factors of the MPS can be used. In some embodiments, the MPS is contained in a tube, column, vial, well plate, container, bottle, drum, porous film, capillary tube, Eppendorf tube (plastic test tube), falcon tube, culture tube, well plates, cuvette or sponge. In other embodiments, the MPS is deposited on paper. In still other embodiments, the MPS is deposited on cloth or string.

Generally speaking, if a combination of multiple phase component phases results in a phase-separated MPS, any sub-combination of the multiple phase component phases will also result in a phase-separated MPS. Thus, if a five-phase component MPS phase-separates, any four-polymer aqueous system selected from the five phase component phases can also phase-separate. Likewise, any two- or three-phase component MPS selected from the five phase component phases can also phase-separate. Other suitable combinations of polymers are contemplated.

In some embodiments, whether or not a MPS comprising multiple phase components will phase-separate can be predicted based on the properties of the MPS containing the sub-combination of the multiple phase components. For instance, phase solutions containing phase components A, B, and C, respectively, will phase-separate and form a three-phase MPS if the phase component A solution and phase component B solution phase-separate, the phase component A solution and phase component C solution phase-separate, the phase component B solution and phase component C solution phase-separate. Similarly, solutions of phase components A, B, C, and D will form a four-phase MPS if the following phase components combinations all phase-separate: A-B-C, A-B-D, A-C-D, and B-C-D. Likewise, solutions of phase components A, B, C, D, and E will form a five-phase MPS if the following phase components combinations all phase-separate: A-B-C-D, A-B-C-E, A-B-D-E, A-C-D-E, B-C-D-E. Also, solutions of phase components A, B, C, D, E, and F will form a six-phase MPS if the following phase components combinations all phase-separate: A-B-C-D-E, A-B-C-D-F, A-B-C-E-F, A-B-D-E-F, A-C-D-E-F, and B-C-D-E-F. The predictions of more complex MPS based on the same principle is contemplated. These predictions have largely been confirmed by experimental data. Certain predicted MPS have not been produced by experiments can be produced via routine experimental optimization.

As used herein, a MPS can be identified by its phase components in the phases of the MPS. For instance, a Ficoll-dextran-poly(2-ethyl-2-oxazoline) system refers to a three-phase MPS, wherein the phase components in each phases of the MPS are Ficoll, dextran, and poly(2-ethyl-2-oxazoline), respectively. Each phase includes a suitable solvent capable of dissolving the phase components. In some instances, a liquid polymer is used and the liquid polymer forms a phase with no solvent added.

In some embodiments, the multi-phase polymer system is provided by mixing suitable polymers or surfactants with a solvent and subjecting the mixture to centrifugation. Any types of centrifugation known in the art can be used in the formation of the MPS. In some embodiments, the MPS is formed using soft centrifugation. Soft centrifugation is described above. In some specific embodiments, the soft centrifugation is achieved by an eggbeater centrifuge. Other methods of soft centrifugation known in the art are also contemplated.

Density-Based Separation Using Multi-Phase Systems

A method of using a MPS comprising two or more phases to separate samples comprising analytes of interest according to the densities is described. In some embodiments, a method of analyzing or separating a sample comprising one or more analytes of interest according to the density of the analytes or the density of other elements comprising the sample using a MPS is used. The method comprises: a) providing a multi-phase system comprising two or more phase-separated solutions, wherein each phase comprises a phase component selected from the group consisting of a polymer, a surfactant and combinations thereof, wherein at least one phase comprises a polymer; each said phase has an upper and a lower phase boundary; and each of the two or more phases has a different density and the phases, taken together, represent a density gradient; and b) introducing a biological sample comprising one or more biological analytes of interest without disrupting the phase-separated solution; and c) allowing each of the biological analytes to migrate to a location in the multi-phase system that is characteristic of its density, wherein during migration the sample contacts one or more of the two or more phases sequentially. The analytes may have different densities. Such differences in density can result in the analyte preferentially accumulating in one of the phases in the MPS or more typically, at a phase interface or boundary. The desired analyte in the sample can then be viewed, wherein information regarding the analyte is obtained based on its location within the multi-phase system. In other embodiments, the analyte is recovered, thus resulting in an improved purity or isolation of such analyte.

In other embodiments, a method of analyzing a sample comprising at least one analyte of interest according to the density of a tagged analyte of interest in an MPS is disclosed.

The method comprises: a) providing a sample comprising at least one analyte of interest; b) combining the sample with a tag molecule to form a tag molecule-analyte adduct having a density different from the density of the analyte; c) providing a multi-phase system comprising two or more phases with clear boundaries, wherein at least one of the phases comprises a phase component, wherein the phase component is selected from the group consisting of a polymer, a surfactant, and combinations thereof; each of the two or more phases has a different density and the two or more phases, taken together, represent a density gradient; and the phases are phase-separated from each other; and d) introducing the sample comprising the tag molecule-analyte adduct to the multi-phase system; and e) allowing the tag molecule-analyte adduct to migrate to a location in the multiphase system that is characteristic of its density, wherein during migration the sample contacts one or more of the two or more phases sequentially and the analyte and the tag molecule-analyte adduct occupy different locations. As used herein, location means a position at, below, or above the interface between phases.

In another embodiment, the method comprises: a) providing a sample comprising at least one analyte of interest; b) providing a multi-phase system comprising two or more phases with clear boundaries, wherein at least one of the phases comprises a phase component, wherein the phase component is selected from the group consisting of a polymer, a surfactant, and combinations thereof; each of the two or more phases has a different density and the two or more phases, taken together, represent a density gradient; and the phases are phase-separated from each other; c) introducing the sample comprising a tag molecule and the analyte to the multi-phase system, wherein the tag molecule and the analyte combine to form a tag molecule-analyte adduct having a density different from the density of the analyte; and d) allowing the tag molecule-analyte adduct to migrate to a location in the multiphase system that is characteristic of its density, wherein during migration the sample contacts one or more of the two or more phases sequentially and the analyte and the tag molecule-analyte adduct occupy different locations.

In another embodiment, a kit for separating a sample comprising one or more biological analytes of interest using a multi-phase system is disclosed. The kit comprises a) two or more phase components selected from the group consisting of a polymer, a surfactant, and combinations thereof; b) optionally a tag molecule capable of binding the one or more biological analytes of interest, wherein the tag molecule has a different density than the biological analyte of interest; and c) instructions for: (i) combining the two or more phase-separated solutions with a common solvent to create a multi-phase system; (ii) optionally, combining the biological analyte of interest and tag molecule, and (iii) separating the biological analyte of interest from the sample.

In one or more embodiments, the kit further comprising an aliquot of a common solvent which, when combined with the two or more phase components, provides a multiphase system.

In one aspect, the kit comprises instructions which direct that the biological analyte of interest be combined with the tag molecule to form a tag molecule-analyte adduct before introduction to the multi-phase system.

In each of these embodiments, the analyte (or analyte-tag adduct) traverses the phase(s) of the MPS sequentially and migrate to a location of MPS corresponding to its density. In this process, the analyte does not have simultaneous contact with two or more phases of the MPS except when passing the interface between two adjacent phases. This method is distinguished from the separation based on affinity as described above in that in the latter, the analyte needs to have simultaneous contact with all of the phases of the MPS so that a thermodynamic equilibrium is reached and the analyte can preferentially reside in one of the phases based on its affinity towards that phase. This process is commonly referred to as 'partitioning' or 'extraction.' In comparison, in the density-based separation as described herein, the analyte migrates through the MPS phase one at a time, contacting one or more of the phases sequentially and eventually arriving at a location in the MPS characteristic of its density. Because the analyte only contacts a single phase at a time, except at the interface where the analyte may contact and interact with two adjacent phases simultaneously, no partitioning or extraction of the analyte into a particular phase is possible.

Each phase of the MPS has an upper and a lower phase boundary, and two adjacent phases forms a common interface in between. In most instances, there is not an exact match between the analyte density and the density of any particular phase. The analyte's density is between the densities of two adjacent phases in a MPS, and the analyte should therefore remain at the interface of the two adjacent phases. If the analyte should have the same density as that of one of the phases, the analyte will remain with in the density-matched phase without contacting any boundary. In this case, the analyte resides within the phase due to a density match and not due to any favorable or preferential interaction of the analyte with one phase over another. In still other embodiments, the analyte may have a density less than that of the top phase of the MPS (the phase with the least density) and remain at the top of the MPS with a portion of the analyte above the upper boundary of the top phase after migration. In still other embodiments, the analyte may have a greater density than that of the bottom phase of the MPS (the phase with the most density) and remain at the bottom of the MPS after migration.

In some embodiments, the analyte is allowed to migrate based on gravity. In other embodiments, the analyte is allowed to migrate using a centrifuge. Non-limiting examples of centrifuge include laboratory centrifuges (using either a fixed angle or swinging bucket rotors) and soft-centrifuges. Soft centrifugation refers the uses of soft tubing, e.g., polyethylene tubing, as the sample container and a simple device as the rotor (see, Wong et al., "Egg beater as centrifuge: isolating human blood plasma from whole blood in resource-poor setting", *Lab Chip,* 2008, 8, 2032-2037). In some specific embodiments, the soft centrifugation is achieved by an eggbeater centrifuge. Other methods of soft centrifugation known in the art are also contemplated.

Migration occurs until the analyte reaches a phase with which it is density matched or a phase of higher density, so that it no longer moves over time through the multi-phase system. This situation is referred to as having reached an 'equilibrium location'. In the case of gravity migration, the time to reach equilibrium migration is in the range of seconds to several days depending on factors such as viscosity, particle size, and buoyant density. Use of centrifugation can accelerate the migration process and reduce the time to reach equilibrium location to minutes or hours. The centrifuge works using the sedimentation principle, where the centripetal acceleration causes more dense substances to separate out along the radial direction (towards the bottom of the tube). By the same token, less dense objects will tend to move to the top. Centrifugation conditions can include speeds ranging from 1 g to over 170,000 g for periods lasting a few seconds to several days. Centrifuges can be used with heating and cooling to, e.g., modify the viscosity of the system or to maintain cell viability. Persons of ordinary skill in the art would know how to adjust these conditions to achieve separation in a given system. For example, speeds and times can be varied depending on the type of analyte sought to be separated (pelleting application), complexity of the sample, or composition of the MPS.

In some embodiments, a two-phase MPS can be used for purposes disclosed herein. In some other embodiments, three or more phase systems are used. It was believed that the inclusion of additional phases may prevent the enrichment of the target molecule in a specific phase, because the target molecule may distribute into the additional phases. This belief may account for the lack of literature regarding these multi-phase polymer systems. Applicants have surprisingly found that broadening the landscape of polymers that exhibit limited interaction in aqueous multi-phase polymer systems provides superior tunability for applications based on differences in density and affinity and finer control over the partitioning of complex mixtures of objects.

The analytes used in the disclosed methods can be biological in origin. The methods disclosed herein can be used for separating biomoleculaes e.g., proteins, saccharides, polyterpenes, polynucleic acids, extracting recombinant proteins, analyzing enzymatic digestions, and partitioning cells. Other uses known in the art are contemplated. Types of biological analytes that can be used include, without limitation, cells, cancer cells, stem cells, cell extracts, tissue extracts, cell organelles, cell fragments, cell membranes, cell membrane fragments, viruses, virus-like particles, bacteriophage, cytosolic proteins, secreted proteins, signaling molecules, embedded proteins, nucleic acid/protein complexes, nucleic acid precipitants, chromosomes, nuclei, mitochondria, chloroplasts, flagella, biominerals, protein complexes, phage, minicells, and protein aggregates, tissues, organisms, small molecules, large-sized molecules, e.g., biomolecules including proteins, and particles. In one or more aspects, the types of cells used in the disclosed methods include mammalian cells selected from the group consisting of gland cells (e.g., exocrine secretory epithelial cells, salivary gland mucous cells, salivary gland serous cells, Von Ebner's gland cells, mammary gland cells, lacrimal gland cells, ceruminous gland cells, eccrine sweat gland dark cells, eccrine sweat gland clear cells, apocrine sweat gland cells, gland of Moll cells, aebaceous gland cells, Bowman's gland cells, Brunner's gland cells, seminal vesicle cells, prostate gland cells, bulbourethral gland cells, bartholin's gland cells, gland of litter cells, uterine endometrial cells, isolated goblet cells, stomach lining mucous cells, gastric gland zymogenic cells, gastric gland oxyntic cells, pancreatic acinar cells, paneth cells, type II pneumocyte cells, and Clara cells), hormone secreting cells (e.g., anterior pituitary cells, intermediate pituitary cells, magnocellular neurosecretory cells, gut and respiratory tract cells, thyroid gland cells, parathyroid gland cells, adrenal gland cells, chromaffin cells, Leydig theca interna cells, corpus luteum cells, granulosa lutein cells, theca lutein cells, juxtaglomerular cells, racula densa cells, peripolar cells, and mesangial cells), epithelial cells lining closed internal body cavities (e.g., blood vessel and lymphatic vascular endothelial fenestrated cells, blood vessel and lymphatic vascular endothelial continuous cells, blood vessel and lymphatic vascular endothelial splenic cells, synovial cells, serosal cells, squamous cells, columnar cells, dark cells, vestibular membrane cells, stria vascularis basal cells, stria vascularis marginal cells, Claudius cells, Boettcher cells, choroid plexus cells, pia-arachnoid squamous cells, pigmented and non-pigmented ciliary epithelial cells, corneal endothelial cells, and peg cells), ciliated cells of the respiratory tract cells, oviduct cells, uterine endometrium cells, rete testis cells, and ductulus efferens cells, ciliated ependymal cells of central nervous system, keratinizing epithelial cells (e.g., epidermal keratinocyte, epidermal basal cells, keratinocytes, nail bed basal cells, medullary hair shaft cells, cortical hair shaft cells, cuticular hair shaft cells, cuticular hair root sheath cells, hair root sheath cell of Huxley's layer, hair root sheath cell of Henle's layer, external hair root sheath cells, and hair matrix cells), wet stratified barrier epithelial cells (e.g., surface epithelial cell of stratified squamous epithelium of cornea, tongue, oral cavity, esophagus, anal canal, distal urethra and vagina; basal cell of epithelia of the cornea, tongue, oral cavity, esophagus, anal canal, distal urethra, and vagina; and urinary epithelium cells), cells of the nervous system (e.g., sensory transducer cells, auditory inner hair cell of organ of corti, auditory outer hair cell of organ of corti, basal cell of olfactory epithelium, cold-sensitive primary sensory neurons, heat-sensitive primary sensory neurons, Merkel cell of epidermis, olfactory receptor neurons, pain-sensitive primary sensory neurons, photoreceptor cells of the retina, proprioceptive primary sensory neurons, touch-sensitive primary sensory neurons, cholinergic neurons, adrenergic neurons, peptidergic neural cells, inner and outer pillar cells, inner and outer phalangeal cells, border cells, hensen cells, taste bud supporting cells, olfactory epithelium supporting cells, Schwann cells, satellite cells, enteric glial cells, central nervous system neural and glial cells, and lens cells), hepatocyte, adipocytes, liver lipocytes, kidney cells (e.g., glomerulus parietal cells, glomerulus podocyte cells, proximal tubule brush border loop of Henle thin segment cells, distal tubule cells, and collecting duct cells), lung cells, Type I pneumocytes, pancreatic duct cells, nonstriated duct cells, principal cells, intercalated cells, duct cells, intestinal brush border cells, exocrine gland striated duct cells, gall bladder epithelial cells, ductulus efferens nonciliated cells, epididymal principal cells, epididymal basal cells, extracellular matrix cells, ameloblast epithelial cells, planum semilunatum epithelial cells, loose connective tissue fibroblasts, corneal fibroblasts, tendon fibroblasts, bone marrow reticular tissue fibroblasts, nucleus pulpous cells, cementoblast/cementocytes, odontoblast/odontocytes, hyaline cartilage chondrocytes, fibrocartilage chondrocytes, fibroblast cartilage chondrocytes, osteoblast/osteocytes, osteoprogenitor cells, hyalocytes of vitreous body of eye, stellate cells of perilymphatic space of ear, hepatic stellate cells, pancreatic stele cells, contractile cells, skeletal muscle cells, heart muscle cells, smooth muscle cells, blood and immune cells (e.g., erythrocyte, megakaryocyte, monocyte, connective tissue macrophage, epidermal langerhans, osteoclast, dendritic cell, microglial cell, neutrophil granulocyte, eosinophil granulocyte, basophil granulocyte, mast cell, T cell, suppressor T cell, cytotoxic T cell, natural killer T cell, B cell, and reticulocyte), Stem cells and committed progenitors for the blood and immune system (e.g., pigment cells, melanocytes, and retinal pigmented epithelial cells), germ cells (e.g., oocyte, spermatid, spermatocyte, spermatogonium cell, and spermatozoon, nurse cells (e.g., ovarian follicle cell, and sertoli cells, and thymus epithelial cells), interstitial cells, and combinations thereof.

In one or more aspects, the type of cell used in the disclosed methods is a plant cell selected from the group consisting of parenchyma cells, chlorenchyma cells, collenchyma cells, sclerenchyma, epidermal cells, cork cells, xylem cells, xylem vessel cells, meristematic cells, and combinations thereof.

In one or more aspects, the type of cell used in the disclosed methods is a protozoan selected from the group consisting of *Amoeba, Paramecium, Euglena*, and combinations thereof.

In one or more aspects, cells used in the disclosed methods are prokaryotic cells selected from the group consisting of bacteria (e.g., bacteria of the phyla Aquificae, Xenobacteria, Fibrobacter, Bacteroids, Firmicutes, Planctomycetes, Chrysogenetic, Cyanobacteria, Thermomicrobia, Chlorobia, Proteobacteria, Spirochaetes, Flavobacteria, Fusobacteria, and Verrucomicrobia), archaea (e.g., Crenarchaeota, Euryarchaeota, Korarchaeota, Nanoarchaeota, Thaumarchaeota, Aigarchaeota), and combinations thereof.

In one or more aspects, the analyte of interest is a virus or virus-like particle selected from the group consisting of dsDNA viruses, ssDNA viruses, dsRNA viruses, (+) ssRNA viruses, (−) ssRNA viruses, ssRNA-RT viruses, dsDNA-RT viruses, and combinations thereof.

In one or more aspects, tissues used in the disclosed methods are mammalian tissues selected from the group consisting of connective tissue (e.g., bone, cartilage, lymphoid tissue, blood, areolar tissue, adipose tissue, elastic tissue, hypodermis, lamina propria, submucosa, mesentery, fascia, muscle capsule, tendons, sclera, and dermis), muscle tissue (e.g., smooth muscle, cardiac muscle, and skeletal muscle), nervous tissue, epithelial tissue (e.g., stratified squamous epithelium, cuboidal epithelium, endothelium, simple columnar epithelium, simple squamous epithelium, mesothelium, pseudostratified epithelium, transitional epithelium, and glandular epithelium), tissues of the eye, ear, and skin, and combinations thereof.

In one or more aspects, the types of tissue extracts used in the disclosed method are extracts from tissues including occular, gingival, heart, liver, brain, stomach, kidney, lung, gall bladder, spleen, intestinal, uterine, prostatic, epithelial, connective, and muscle tissues.

In one or more aspects, tissues used in the disclosed methods are plant tissues selected from the group consisting of vascular tissue, dermal tissue, ground tissue, meristematic tissue, and combinations thereof.

In one or more aspects, the types of organisms used in the disclosed method include parasites. In one or more aspects, the parasite is a worm. Non-limiting examples of worms that can be separated from biological samples include flat worms such as flukes and tape worms, or roundworms such as eye worms, filarial worms, *Trichinella* roundworms, hookworms, annelids ("ringed worms") such as leeches, and ascarids. In another aspect, the disclosed methods can be used to separate parasitic insects from samples. Non-limiting examples of such insects include mosquitoes, fleas, lice, ticks and mites.

In one or more aspects, the disclosed method is used to analyze biological carriers, including without limitation, food, juice, milk, whole blood, plasma, serum, sweat, feces, urine, saliva, tears, vaginal fluid, prostatic fluid, gingival fluid, amniotic fluid, intraocular fluid, cerebrospinal fluid, seminal fluid, sputum, ascites fluid, pus, nasopharengal fluid, wound exudate fluid, aqueous humour, vitreous humour, bile, cerumen, endolymph, perilymph, gastric juice, mucus, peritoneal fluid, pleural fluid, sebum, vomit, and combinations thereof. In such biological carriers, it is possible to identify the presence or absence of cells, cellular components, large biomolecules or other components that can be an indication of disease, genetic condition or infection.

Samples can be introduced to the MPS in the form of a solution or suspension of material. Non-limiting examples of ways in which these samples can be added to the MPS include by pour, pipette, injection, drip, siphon, capillary action, spray, aspiration followed by expulsion, and pump.

Because the separation is carried out using gravity (enhanced gravitational force using centrifugation), the analyte is desirably in suspension in the MPS phases, e.g., the analyte is insoluble in the MPS phases. In addition, separation will be achieved more readily and in a shorter time frame for larger analytes. Without additional modifications, such a density tagging, biomolecules of a size such that their interactions in solution are predominantly gravity driven can be distinguished in the MPS system. When analytes are sufficiently small, the molecular forces (electrostatic, Van der Waals, etc) are sufficient strong relative to the size and mass of the analyte that the interaction with the solvent is dictated by these forces. Such analytes are capable therefore of partitioning selectively into one or another phase due to favorable molecular interactions that effectively disregard the densities of the analytes. In most instances, the analyte has at least one dimension that is greater than 200 nm, or greater than 500 nm, or greater than 1 µm, which is sufficient for gravitation forces to predominate.

In embodiments in which the sample comprises small particles that are of interest, the samples can be subjected to aggregating agents to induce aggregation of the small particles, so that the analyte is larger and can be separated readily using MPS, or the densities of the small particles can be modified using additives to force their migration to different locations in the MPS such that the aggregated small particles pass through one or more phases sequentially. Non-limiting examples of small particles that require aggregation include multivalent particles (e.g., viruses, cells, and any basic unit that expresses surface markers), platelets (adenosine diphosphate), and erythrocytes (hemagglutinin or concanavalin A), As a result of the disclosed methods, one or more analytes of interest may preferentially accumulate in one of the phase or at an interface in the MPS, while another analyte, impurity or object in the sample containing the analyte may preferentially accumulate in another phase or interface of the MPS. The desired analyte in the sample can be visualized after separation via a variety of methods. Firstly, separation of some analytes can visualized by human eye. Those that are not readily visible by the eye can be visualized using methods known in the art. For example, separation can be visualized with the aid of a microscope, scanner, magnifying glass, fluorescence (e.g., fluorescein, rhodamine, and diamidino-2-phenylindole) and dye (e.g. crystal violet, methylene blue, and acid orange). In addition, for embodiments in which the analyte is a cell, a cell suspension can be incubated in a solution of antibodies labeled with fluorophores specific for cell type separated using the disclosed methods. In another aspect in which the analyte is a bacterium, a suspension of bacteria can be incubated with bacteriophage (a species-specific virus) that are genetically modified to produce a fluorescent protein (e.g., red fluorescent protein) within the bacterium.

In some embodiments, it will be sufficient to simply observe the location of the analyte in the multi-phase system in order to obtain useful information. For example, a biological sample such as blood, urine or feces can be subjected to analysis by MPS in order to determine the presence or absence of certain markers that can be an indication of disease, genetic disorder or infection. For example, the cellular components of blood can be separated by MPS (Blood plasma has a density of about 1.025 g/cm$^3$ and red blood cells have a density of approximately 1.100 g/cm$^3$. There is some debate regarding the actual density of erythrocytes, however they have been described with a narrow distribution of densities, which makes detection of shifts in density useful for assessing blood cell health.). The presence of blood disorders, such as sickle cell anemia, can be inferred by the presence of an analyte at a boundary that is specific to the density of sickle cell erythrocytes as compared to healthy erythrocytes. Similarly, a urinary infection could be detected by noting the presence of analyte at a boundary that is selective for white blood cells. Differences in densities that can be detected can be 0.001 g/cm$^3$ or more, which is sufficient to detect such density differences. Non-limiting examples of tests that require only information about the location of the analyte in the MPS include white blood cells in urine, sickle cell erythrocytes, parasitized cells, parasitic organisms, and the presence or absence of rare cells, diseased cells, foreign cells, bacteria, yeast, fungi, or viruses.

MPS are selected to have phases with densities that are capable of distinguishing between the analyte of interest and other components of the sample. For the separation of blood plasma and red blood cells, for example, phases having densities that are (1) less than blood plasma, (2) greater than blood plasma, but less than red blood cells and (3) greater than red blood cells could be used to separate plasma cells and red blood cells into two different boundary locations. A number of MPS systems with a range of densities are known and can be used to practice the methods of the invention. See, PCT Patent Application No. PCT/US2011/048673, filed on Aug. 22, 2011, entitled "MULTIPHASE SYSTEMS AND USES THEREOF".

In other embodiments, the desired analyte in the sample can be recovered by retrieving the phase in which the analyte preferentially has accumulated, thus resulting in an improved purity of such analyte. Analytes can be recovered from the system using extraction methods known in the art. In several aspects of one or more embodiments, analytes retained in gradients can be recovered using a fractionator, pipette, drip method, side-puncturing a tube, or combinations thereof. In one aspect, a fractionator can be used to carefully control the pressure on the liquid and pull known volumes of the gradient in certain increments. The drip method can also be used to extract separated analytes. The bottom of a tube is punctured and allowed to drip into sample tubes. This method, like the fractionator method, is ideal for systems such as the disclosed MPS that form clear visual interfaces that can be observed by eye. In another aspect, a pipette is introduced to the top of the sample to remove most, but not all, of the top layer without pulling too close to the interface. Once the top layer is mostly removed, a clean pipette tip can be inserted from the top layer into the second layer. Light agitation of the tip can be used to clear the interface from the tip. The desired layer can then be drawn up in the pipette. The interfaces above and below the desired layer should not be drawn up with the desired layer to avoid layer contamination. In yet another aspect, a plastic tube is side punctured one or more times using a needle, such as a 21 to 16 gauge needle, to puncture the tube at the desired phase. The desired phase is pulled from the tube volume. In each of these aspects, if the analyte of interest is in a phase, the interfaces above and below the phase should not be disturbed to avoid layer contamination. Similarly, if the analyte of interest is in an interface, the phases above and below the interface should not be disturbed to avoid layer contamination.

The MPS system can be designed to separate living cells or other biologically sensitive biological systems, e.g., ova, worms, parasites, insects, protozoa, arachnids, fungi, annelids, and arthropods, without harm to the living system. An MPS system designed to separate biologically sensitive systems may include without limitation GRAS polymers, biocompatible salts, isotonicity with blood plasma, reagents that maintain the viability of separated cells or are used to probe the activity of separated cells, lytic or non-lytic reagents, biocompatible buffer conditions that maintain a physiological pH, and dyes or stains to label analytes and enhance detection.

In one aspect of one or more embodiments, analytes of interest can be tagged to alter their density. Analyte tags can be used for example to assist in the separation of analytes having the same or substantially same density as other objects or impurities in the sample. The sample components can be separated according to their densities when the analytes of interest, other objects or impurities are tagged. For example, the analyte of interest can have a binding affinity for the tag molecule such that the analyte of interest and the tag molecule link to form a tag molecule-analyte adduct. The tag molecule-analyte adduct forms when the tag molecule covalently bonds, non-covalently bonds, hybridizes, complexes, or conjugates with the analyte of interest. Tags can include beads of higher or lower density to that of the analyte that have been treated to provide a chemical surface that can interact with the analyte. Polymer beads, metal beads or glass beads having a range of densities can be chemically modified, for example with one of biotin or avidin, antibodies and the like. The complementary surface on the analyte of interest, will cause the analyte to bind to the bead surface. A non-limiting example of using an adduct to separate analytes of like density includes the use of antibodies, conjugated to gold colloids, that are specific for cell markers expressed by a single desired cell type within a range of densities that capture a variety of cell types such as, e.g., separating CD4+ T cells from a mixture of leukocytes of equivalent density. Other non-limiting examples of using an adduct to separate analytes of like density include separating antigen-presenting cells for antigen analysis for vaccine development, differentiating hematopoietic stem cells CD34+ and CD38−, differentiating cultured stem cells from feeder cells in stem cell therapies, and distinguishing pathogenic and non-pathogenic particles based on surface markers indicative of virulence (e.g., distinguishing pathogenic *E. coli* from non-pathogenic strains based on the presence or absence of the surface marker intimin). Tags can also include larger biomolecules that have affinity for the analyte of interest. Upon binding, the density of the analyte is altered.

Biological carriers can also be separated from each other, or from other objects or impurities in the sample, using the methods disclosed herein. For example, complex biological carriers that contain a variety of components can be screened for the presence or absence of certain components that are useful for health and public safety. MPS screening can be used to examine food for adulteration, confirm presence or absence of heavy metals in foods, screen bodily fluids such as blood, feces, saliva and urine for the presence of parasites or infection.

In one aspect, the disclosed methods can be used to analyze or separate cell lysates. Cells can be lysed while in the MPS, or they can be lysed and later introduced to the MPS. Cells can be lysed using methods known in the art. For example, cells can be lysed in the MPS by treating the MPS with additives or agents, such as hypotonic buffers that disrupt cell membranes or cause cells to swell and burst. Lysozyme can be used to digest cell walls to free and subsequently separate cellular components of bacteria and yeast based on their densities using a MPS. Cells can also be lysed using other methods, including but not limited to, the addition of lytic agents including some surfactants, manual grinding, liquid homogenization, sonication, and freeze/thaw methods. Manual grinding using mortar and pestle is commonly used to disrupt plant cells. Plant tissue can be frozen in, e.g., liquid nitrogen, and then crushed and ground using a mortar and pestle to lyse cells. Other mechanical methods of mechanical disruption include blenders. Blenders can be used, for example, to grind and disperse large amounts of tissue such as muscle and organs. For smaller samples and cultured cells, liquid-based homogenization can be used to lyse cells. Examples of liquid homogenizers include Dounce homogenizers, Potter-Elvehjem homogenizers, and French presses. Sonication, which uses high frequency sound waves to agitate and lyse cells, can be used to lyse small volumes of cells, bacteria, and thinly sliced tissue samples. The freeze/thaw method can be used to disrupt many types of cells, including mammalian and bacterial cells.

In other embodiments, the disclosed methods can be used to distinguish normal cells from parasitized, infected, rare, and tumor cells. For example, cells infected by viruses or parasites have densities that are either the same or different than normal cells, depending on the type of virus or parasite with which the cell is infected. Samples containing infected cells having different densities than normal cells can be separated from other objects or impurities in the sample using the disclosed methods to separate infected cells from normal cells. For example, cells infected with malaria lose density as the infection progresses. Thus, in some embodiments, an aqueous multi-phase polymer system comprising two or more polymer aqueous solutions or phases is used to isolate malaria-infected blood cells.

Examples of Density-Based Separation Using Multi-Phase Systems

EXAMPLE 1

The layers of an aqueous multiphase system are ordered according to density, and therefore can be used to achieve density-based separation 23 polymers and 11 surfactants were investigated for their ability to promote phase separation in aqueous solutions. These reagents were used as prepared by the commercial manufacturer without further purification, and the molecular weights of the polymers used were polydisperse. For example, the polydispersity index of the poly(2-ethyl-2-oxazoline) species used for these assays is ~3-4 for a molecular weight of 200 kDa. $D_2O$ as a co-solvent or salts were added to affect phase density.

Two-component mixtures of the polymers and surfactants were prepared and selected for screening by vortexing equal volumes of stock solutions at high concentrations for 30 seconds to ensure complete mixing. The mixtures were then centrifuged for five minutes at 2000 g. A visually discernible interface characterized those mixtures that separated into discrete phases, while miscible solutions resulted in a homogenous solution. A number of mixtures resulted in the formation of either a gel or a precipitate, which were considered distinct from those mixtures that generated two liquid phases. Dispersed surfactant micelles also were not considered to be a unique phase in the context of this experiment.

An ordering system based on this empirical miscibility data and consistent within the set of reagents used in this experiment was developed. A series of miscibility profiles was generated for each reagent by assigning a 34-component vector describing the results from all two-component mixtures that include the reagent. The vector has values '0' for mixtures that resulted in homogeneous solutions (miscible), '1' for mixtures that resulted in a precipitate or a gel (incompatible), and '2' for mixtures that resulted in phase separation (immiscible).

The miscibility profiles of N reagents and clusters of reagents can be compared by analyzing the magnitudes of each vector and the distances between vectors in N-dimensional space: a small distance between vectors indicates similar miscibility profiles. Referring to FIG. 12, reagents were ordered in the matrix according to this vector analysis.

Using this approach to ordering, several patterns were identified based on similarities in miscibility in two-component mixtures: neutral, branched polysaccharides (numbers 3 and 4), acrylic acids (4 and 5), cationic species (10, 12, and 13), hydrophobic species incorporating ethylene oxide units (14-18), and anionic species (21, 22, 24, 26-29) are clustered by patterns of miscibility using our analysis.

EXAMPLE 2

The aqueous multi-phase polymer systems used to isolate malaria-infected blood cells are exemplified by the poly(ethylene glycol)-dextran, dextran-Ficoll systems, and systems containing poly(2-ethyl-2-oxazoline), poly(vinyl alcohol), Ficoll, poly(ethylene glycol), dextran poly(2-vinylpyridine-N-oxide), cellulose derivatives, polyvinylpyrrolidone, and combinations thereof.

Malaria is traditionally diagnosed by combining the observation of physical symptoms (i.e., a sustained fever) with confirmation of parasitemia by microscopy. Malaria, however, is most prevalent in rural regions of developing nations where limited access to trained physicians and suitable clinical laboratory equipment hinders the traditional diagnostic approach. Availability of a low-cost, point-of-care test for diagnosing malaria would significantly reduce the burden of this disease in the developing world.

The method of separating analytes in a sample is demonstrated in a specific embodiment in which an aqueous triphase polymer system is used to separate malaria-infected erythrocytes in whole blood from healthy blood cells based on their different densities. This AMPS comprises a mixture of poly(vinyl alcohol) (PVA), poly(ethylene glycol) PEG, and dextran. The density barriers at the polymer/polymer interface of the triphasic PVA/PEG/dextran system were established using the eggbeater centrifuge and were designed to isolate white blood cells at the PVA/PEG interface, infected red blood cells at the PEG/dextran interface (, and healthy red blood cells in the pellet from whole blood. The healthy red blood cells have a density of $\rho \approx 1.100$ g/cm$^3$ and the red blood cells infected with malaria parasites have a density of $\rho \approx 1.080$ g/cm$^3$. Each polymer/polymer interface was designed to isolate a specific component of blood: the 10 wt/vol. PVA ($\rho = 1.022$ g/cm$^3$)/40 wt % PEG ($\rho = 1.067$ g/cm$^3$) interface models the capture of white blood cells, the 40 wt % PEG/30 wt % dextran ($\rho = 1.101$ g/cm$^3$) interface models the capture of malaria-infected red blood cells, and all healthy red blood cells are expected to sediment to the distal end of the tubing. Thus, the blood cells can be separated based on their small difference of densities, which provides a quick and easy identification method of malaria infection.

The PVA/PEG/dextran system described above is used herein to demonstrate the concept of separating malaria-infected blood cells from the healthy blood cells using density standards which represent the density of the malaria-infected blood cells and of the healthy blood cells. In another embodiment, the malaria-infected blood cells can be separated from the healthy blood cells using an ATPS comprising dextran/Ficoll and/or PVA/dextran/Ficoll. The use of any one of the AMPSs disclosed herein to separate malaria-infected blood cells from the healthy blood cells is contemplated.

Figure 6:
FIG. 6 shows the result of a separation of malaria-infected red blood cells from healthy red blood cells.

Referring to FIG. 6, an image of a separation achieved using a two-phase aqueous polymer system comprising layers of dextran and Ficoll to separate a mixture of red blood cells into two populations by centrifugation is shown. The result of this separation is shown in FIG. 6. Red blood cells infected with the malaria parasite *Plasmodium falciparum* (6% of cell population) were concentrated at the interface between polymer layers (see FIG. 6) and healthy red blood cells (94% of cell population) were sedimented through both polymer layers (see FIG. 6). Applicants designed the polymer system such that their densities (1.079 g/cm$^3$ and 1.085 g/cm$^3$, respectively) would selectively facilitate the separation of the two cell types in the sample. Each layer was isotonic with respect to human plasma (300 mOsm/kg) and at physiological pH (7.40).

Figure 7:
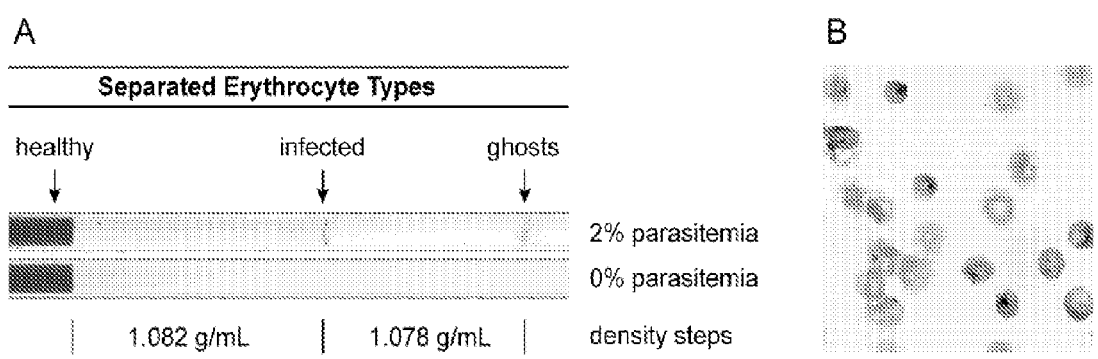
FIG. 7 A-B shows separation of erythrocytes using a two-phase AMPS as a malaria diagnostic.
Figure 8:
FIG. 8 shows fluorescent images of CD4+ T cells (black) in capillary tubes (~20 µL total volume: 10 µL polymer system+10 µL cell sample) labeled with a fluorescein-conjugated antibody to CD4 in a two-phase system centrifuged at 16000 g for 2 minutes; cells that were more dense than both phases sedimented to the bottom of the capillary tube (A); cells with a density between the densities of the two adjacent phases were captured at the interface between phases (B).
Figure 8:
Figure 9:
FIG. 9 shows a series of fluorescent images of two phase systems with *E. coli* that has been genetically modified to express red fluorescent protein (RFP); bacteria were captured at the interface (tubes 1-3) or at the bottom (tubes 4-5).
Figure 10:
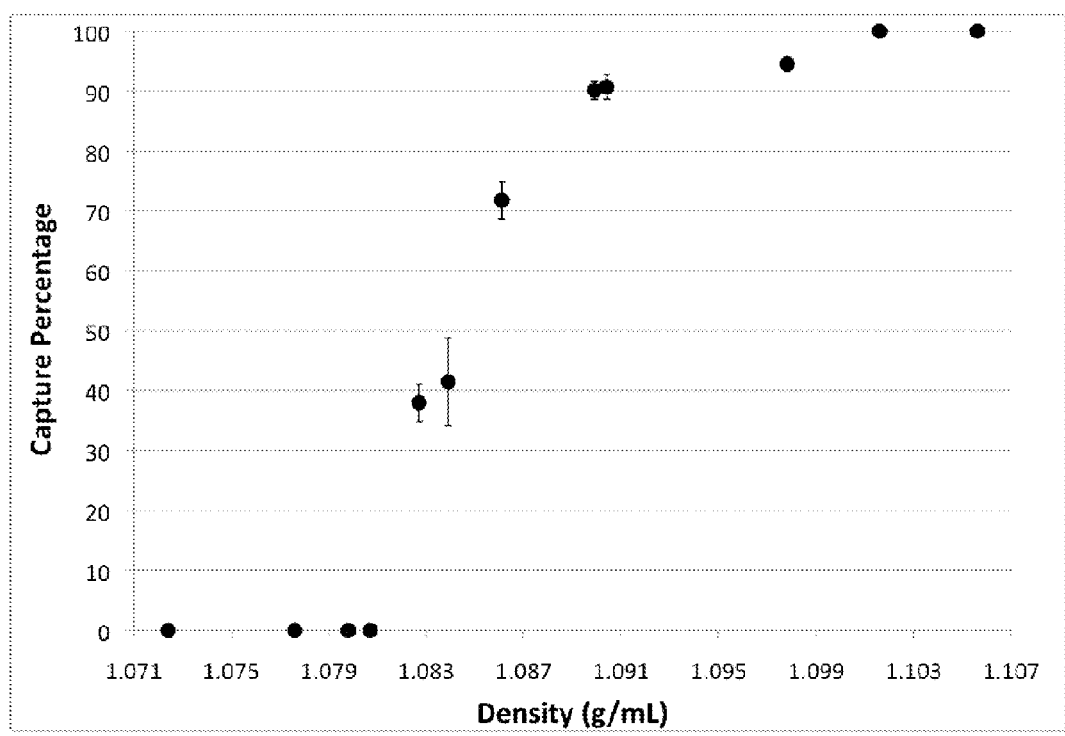
FIG. 10 is a graph (n=7) of interface capture percentage as a function of the density of a lower phase for erythrocytes, which allows densities of cell types to be determined for designing MPS to separate cell types selectively based on density.
Figure 11:
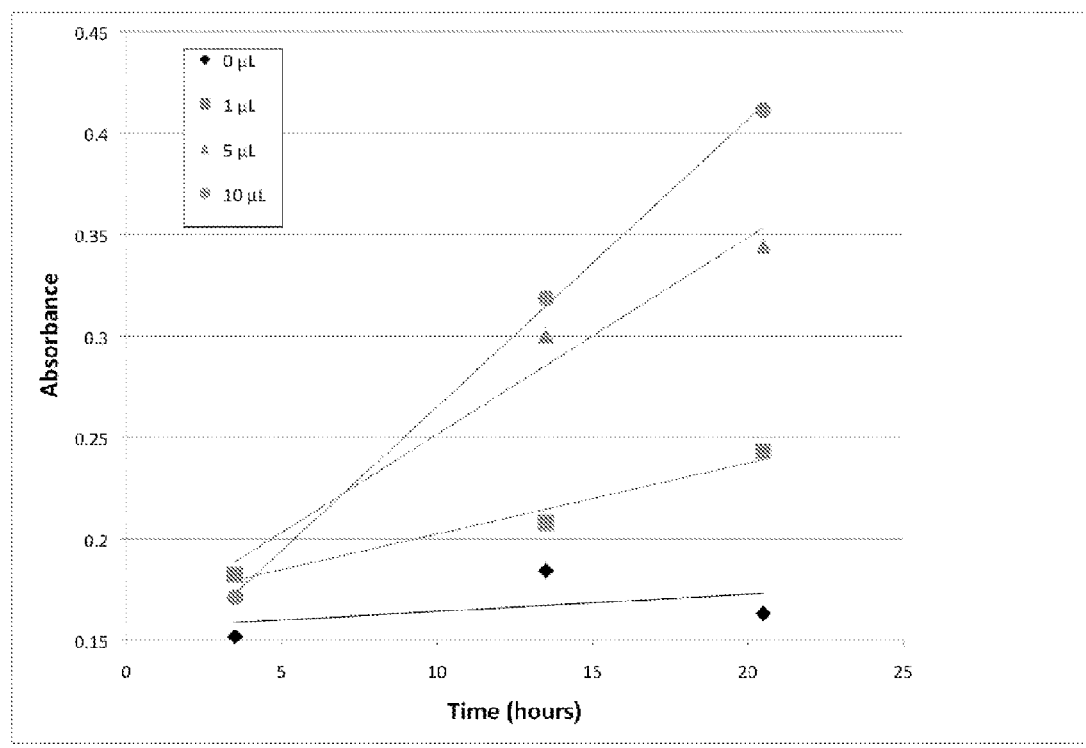
FIG. 11 is a graph (n=3) showing the metabolic activity of MD-MBA-231 breast cancer cells as a function of time and concentration after separation using AMPS.

FIG. 7 shows parasitized from healthy erythrocytes. This figure shows separation of erythrocytes in which a two-phase AMPS was used as a malaria diagnostic. Panel A of FIG. 7 shows images of capillaries that were used to compare the separation patterns of ring stage parasitized erythrocytes and healthy erythrocytes. The presence of a red band at the interface indicated the capture of parasitized cells, thus diagnosing malaria infection. Also referring to FIG. 7, Panel B shows an image from a micrograph of cells were isolated from the AMPS interface after smearing and staining. This panel depicted the near complete enrichment of parasitized erythrocytes due to density-based separation by AMPS.

EXAMPLE 3

Figure 3:
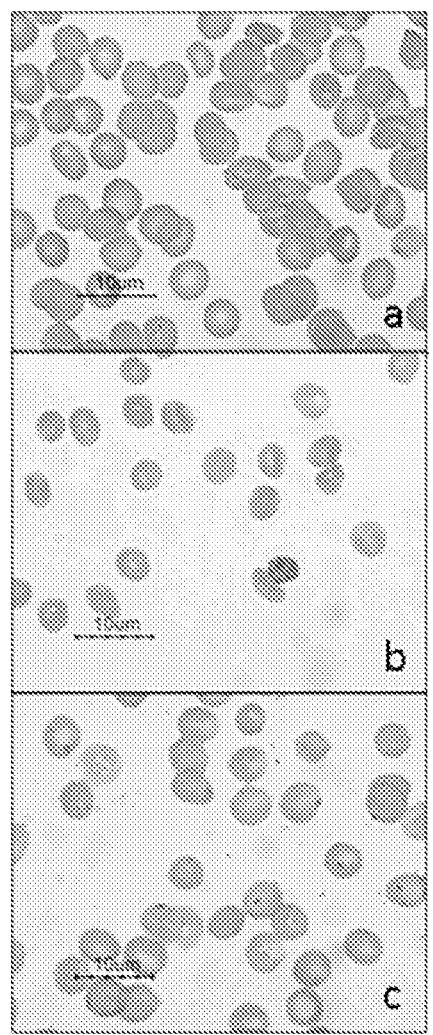
FIG. 3 A-C is an image showing the separation of whole blood into erythrocytes, leukocytes, and cell debris at interfaces of the MPS.

The following example demonstrates that living cells can be separated from a biological carrier, without affecting the viability of the living cells. The analyte can be extracted or removed for further investigation, e.g., culturing, quantifying the results, etc. FIGS. 3A-C show smears from cultures of *P. falciparum*-infected erythrocytes after separation from lymphocytes from human whole blood.

The cultures were separated using a two-phase PEG/Ficoll system. The system was prepared using dextran 500K at 20% (w/v), Ficoll 400K at 23.5% (w/v) with 3 mM Na2 EDTA at a pH of 7.40. NaCl was added to achieve an osmolality of 295 mOsm+/−15. The two phase system was formed and the phases were separated. The phases were then introduced by pipette into a hematocrit tube. 7 microliters of the bottom phase was followed by 7 microliters of the top phase, followed by 7 microliters of the sample (RBCs or parasitized RBCs). The samples were washed with buffer once before introduction to the system. The system was sealed and spun in a hematocrit centrifuge at 13,000 g for 2 minutes after which a clear difference was observable.

The erythrocytes were studied for two days after infection. FIG. 3(A) is an image of the infected erythrocytes on the same day as separation. At this stage, the infection is predominantly at the ring stage and early trophozoites. FIG. 3(B) shows the progress of the infection one day after separation (predominantly late trophozoites and schizonts). Referring to FIG. 3(C), two-days after separation predominantly shows rings and early trophozoites in newly infected cells.

EXAMPLE 4

Separation of small samples can be visualized without disturbing the density of the system using dyes or fluorophores.

Figure 2:
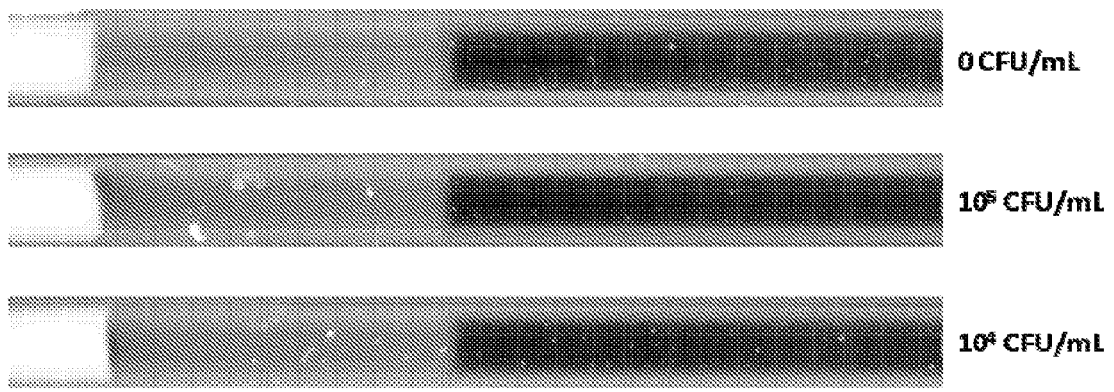
FIG. 2 shows separation of $E.\ coli$ from human whole blood amplified by crystal violet A PEG/Ficoll system with density steps at approximately 1.028 and 1.096 g/mL, which separated the denser $E.\ coli$ from the human blood components.

Referring to FIG. 2, crystal violet was used to visualize small amounts of *E. coli* filtered out of the blood. The *E. coli* were prepared using standard methods. *E. coli* (laboratory strain BL21(DE3)pLysS) were incubated overnight at 37° C. in Lauria-Bertani nutrient broth supplemented with 34 μg/mL of chloramphenicol. A PEG/Ficoll system with density steps at approximately 1.028 and 1.096 g/mL separated the denser *E. coli* from the human blood components. The system was prepared with PEG 20K at 15% mixed with Ficoll 70K at roughly 30%. The solutions were mixed and the emulsion was adjusted to pH 7.40 and NaCl was added to bring osmolality to 295 mOsm+/−15. Once the *E. coli* were introduced to the system, the system was centrifuged at 13,000 g for 4 minutes.

The crystal violet dye allowed a smaller concentration of *E. coli* to be detected by eye than un-stained bacteria (compare to FIG. 1). To achieve the separation shown in FIG. 2, the two phase PEG/Ficoll system was premixed and separated out. Then, 5 microliters of the bottom phase, 5 microliters from the top phase, 5 microliters of crystal violet dye, and 5 microliters of sample blood (*E. coli* doped or control) were added to a tube which was sealed and centrifuged to arrive at the separation depicted in FIG. 2.

EXAMPLE 5

This example demonstrates the separations of components of a biological fluid.

Figure 4:
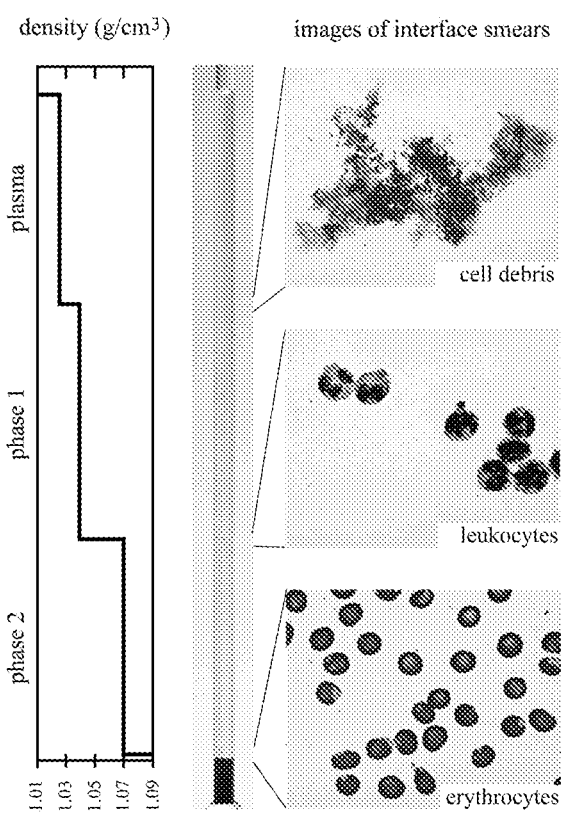
FIG. 4 shows images of a two-phase PEOZ/Ficoll system used to separate cells and plasma from whole blood.
Figure 5:
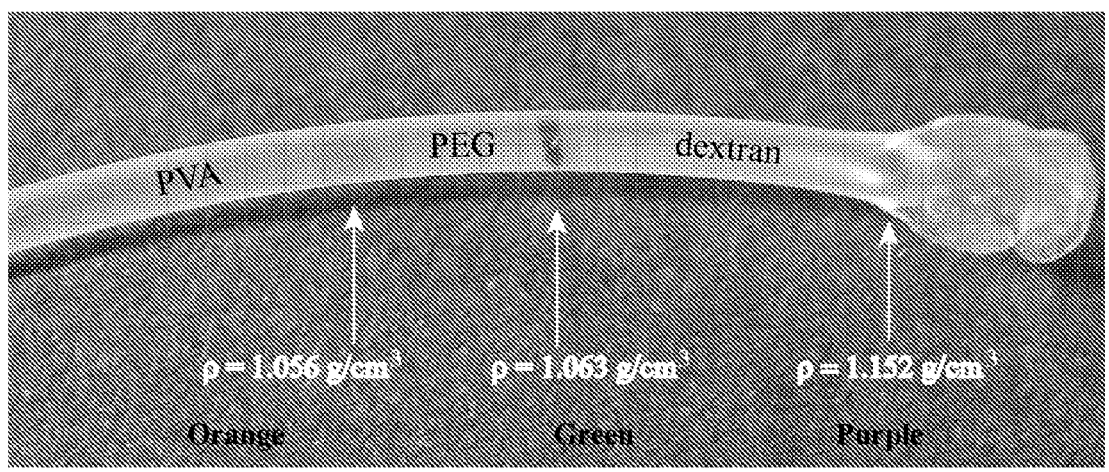
FIG. 5 shows an image of dyed density standards banding at the polymer/polymer interface of the triphasic poly(vinyl alcohol)/poly(ethylene glycol)/dextran system.

Referring to FIG. 4, a two-phase PEOZ/Ficoll system was used to separate cells and plasma from whole blood. A capillary was used to separate components of whole blood by density (center). An illustration of the density step is also shown (left). The system was prepared with PEOZ 50K at 20% with Ficoll 400K at 20%. pH 7.35 and osmolality around 350 mOsm. (In other embodiments, the system is prepared with a PEG 20K 15%/and Ficoll 70K at 12.5% at a pH of 7.40.) 30 microliters of the mixed two-phase system was added to a capillary tube that was capped and spun for 15 minutes to achieve phase separation. The tube was uncapped to add 20 microliters of blood, re-capped, and spun for 14 minutes at about 2000 g in a swinging bucket table top centrifuge. The tubes were cut and sections were removed to make smears for slides. Brightfield microscope images showed smears from isolated sections of the capillary tube dyed with two-part stain (FIG. 4, right) in which erythrocytes, leukocytes, and cell debris were shown to separate and migrate to different parts of the MPS based on each component's density.

EXAMPLE 6

The methods disclosed here combine the portability and simplicity of the soft centrifuge with aqueous multiphase density barriers generated from polymers that exhibit limited interaction. Aqueous polymers that exhibit limited interaction have numerous advantages over discontinuous density gradients for field use: they are easily prepared, owing to the nature of their clear boundaries; they are stable, and thus amenable to long term storage; and they are versatile in that can be altered (composition and/or density) to suit the application.

Moreover, the soft centrifugation assay requires no more than 10 μL of whole blood (easily obtained from a single fingerstick), and rapidly separates blood components. In some embodiments, the soft centrifugation takes 10 minutes or less.

Examples of Separating Tagged Analytes Using Multi-Phase Systems

The density of analytes can be modified using tag molecules. Tag molecules change the density of tagged species by either increasing or decreasing the density of the tagged species. Non-limiting examples of particles that can be used to tag analyte include gold colloids, which increase the density of a tagged species, and hollow glass spheres, which decrease the density of a tagged species. Particles of varying sizes can be used depending on the magnitude of the desired density shift. Sizes ranging from 5 nm-50 μm are contemplated.

Tag molecules can be formed a variety of ways. Non-limiting examples for forming tag molecule include conjugating a dense particle directly to a ligand capable of binding the surface of an analyte of interest (e.g., labeling an antibody to CD4 with a gold colloid), and introducing to the sample a particle capable of binding a ligand without interfering with the ligand's ability to bind to the analyte of interest (e.g., a streptavidin-coated gold colloid capable of binding a biotinylated antibody to CD4).

The tag molecule-analyte adducts can be formed by several methods. The formation of the tag molecule-analyte adduct can be performed in a stepwise manner (e.g., incubating the dense particle with the ligand to form a complex (tag molecule) that is incubated with the analyte of interest before introduction to the MPS, or incubating the analyte of interest with the dense particle and ligand to form a tag molecule-analyte adduct before introduction to the MPS). In another aspect, the tag molecule-analyte adduct is formed when the analyte of interest is introduced to a MPS in which the tag molecule is admixed with one or more phases.

In one or more embodiments, phases comprising phase components such as salts or surfactants that attract or repel tagged analytes of interest cause the tagged analytes to preferentially accumulate in one of the phase or at an interface in the MPS by passing through one or more phases sequentially, while other impurities or components in the sample preferentially accumulate in another phase or at another interface of the MPS, thus separating the tagged analytes from the rest of the sample. In one aspect, this embodiment can be used to separate analytes of interest from samples comprising impurities with densities similar to that of the analyte of interest. In this aspect, the analyte of interest is linked to the tag molecule to form a tag molecule-analyte adduct having a density that is different than the density of the impurity, other objects in the sample, any untagged analyte, or combinations thereof. The MPS has one or more phases or phase components to which the analyte, impurity, other objects, and/or untagged analyte preferentially migrate. The MPS has one or more phase components consisting of surfactant, polymer, or both. The tag molecule-analyte adduct can then be separated from the impurity, other objects, or untagged analyte by adding the sample to the MPS. Because the tag molecule-analyte adduct has a density that is different than the density of the impurities, other objects, or untagged analyte the tag molecule-analyte adduct and impurities separate and move to different locations in the MPS by passing through one or more phases sequentially.

In some aspects, the disclosed methods for analyzing and separating samples can be used to determine whether a sample contains cells infected by a particular infectious agent using tag molecules that are attracted to or repelled by phases containing certain phase components. For example, cells infected by viruses produce viral proteins, some of which migrate to the cell's outer membrane where the proteins form a complex that identifies the cell as infected. Tag molecules that preferentially link to membrane proteins characteristic of a certain virus can be introduced to a sample that may or may not contain cells infected by that virus. For example, a sample that may contain a certain virus can be contacted with a tag molecule specific for a particular viral protein. The tag molecule changes the density of the tagged virus such that it has a different density than other objects or impurities in the sample. If the virus is present in a sample, the viruses are tagged with the tag molecule. When the tagged viruses are introduced to the MPS, the tagged virus preferentially migrates to a particular phase or phases based on its density, passing through one or more phases sequentially until it eventually comes to rest in a phase or at an interface with the same density as the tagged virus. The phase, phases, or interface containing the tagged virus can optionally be separated from the system to further separate or analyze the tagged virus.

Similarly, in another embodiment, the disclosed methods can be used to determine whether a sample contains rare cells such as activated lymphocytes, stem cells, fetal cells and tumor cells. In still another embodiment, the disclosed methods can be used to distinguish benign tumor cells from cancer cells. Cells use signaling proteins to respond to their environment. For example, many tumor cells, including cancer cells, have membrane proteins that are characteristic of the type of tumor or cancer that has affected the cell. In these embodiments, a tag molecule capable of linking to the membrane protein can be selected provided the tag molecule gives the cell affected by tumor or cancer a different density compared to normal cells. The tag molecule is also selected based on its ability to link to the membrane protein on the infected cell. The tag molecule can be linked to the membrane protein by covalent bonding, non-covalent bonding, hybridization, electrostatic interactions, complexing, and conjugation to form a tag molecule-analyte adduct. The sample containing the tag molecule-analyte adduct can be added to the MPS, and because the density of the tag molecule-analyte adduct (i.e., tagged, infected cell) is different than the density of normal cells, infected cells that have been tagged and normal cells will move to different locations in the MPS passing through one or more phases sequentially. Similarly, tag molecules specific to membrane proteins characteristic of other rare cells such as stem cells, activated lymphocytes, and fetal cells can be used according to the methods disclosed herein to separate tagged rare cells from normal cells.

EXAMPLE 7

Samples containing cells of interest that have the same density as other cells in the sample can be tagged to separate the cell type of interest from the rest of the sample using density-based separation in a MPS.

CD3−/CD4+ cells are separated from a co-culture of T cell lymphocytes containing CD3+/CD4− and CD3−/CD4+ cells. The cells are cultured using standard methods. The density of each cell type are determined using a MPS, and are found to be identical ($\rho=1.055$ g/cm$^3$).

1 mg/mL streptavidin-coated 50 nm gold nanoparticles are incubated with 100 μg/mL biotinylated antibody to CD4 for 2 hours in isotonic PBS buffer to form an immunocomplex solution.

The cells are harvested from the culture by centrifugation at 4000 g for 2 minutes. The supernatant is removed and the cells are resuspended in an amount of cell culture medium sufficient to double the cell concentration. The cells are diluted 1:1 with the immunocomplex solution and incubated for 1 hour.

The cells are introduced to a two-phase MPS and sedimented by centrifugation at 4000 g for 10 minutes. The MPS separates the cells into three populations: cell debris (top of system); CD3+/CD4− T cells (interface between phases); and tagged CD3−/CD4+ cells (bottom of the system). The tagged CD3−/CD4+ cells are isolated by pipette and resuspended in cell culture medium for further analysis or culturing.

Upon review of the description and embodiments of the present invention, those skilled in the art will understand that modifications and equivalent substitutions may be performed in carrying out the invention without departing from the essence of the invention. Thus, the invention is not meant to be limiting by the embodiments described explicitly above, and is limited only by the claims which follow.

What is claimed is:

1. A method of analyzing or separating a sample comprising one or more biological analytes of interest using a multiphase system, comprising:

a) providing a multi-phase system comprising two or more phase-separated solutions having a stable interface between adjacent phases, wherein the two or more phase-separated solutions comprise
a first phase solution comprising a first phase component predominantly residing in the first phase solution; and
a second phase solution adjacent to the first phase solution and comprising a second phase component predominantly residing in the second phase solution, said second phase component different from the first phase component;
wherein the first and second phase solutions have a common solvent and each of the first and second phase components is selected from the group consisting of a polymer, a surfactant and combinations thereof, wherein at least one of the first and second phase components comprises a polymer;
each said phase has an upper and a lower phase boundary; and
each of the two or more phases has a different density and the phases, taken together, represent a density gradient;
b) introducing a biological sample comprising one or more biological analytes of interest without disrupting the phase-separated solution; and
c) allowing the biological analyte to migrate to a location in the multi-phase system that is characteristic of its density, wherein during migration the analyte contacts one or more of the two or more phases sequentially such that the analyte's final position in the system is not determined predominantly by partitioning.

2. The method of claim 1, wherein the multi-phase system further comprises one or more additional phases selected from the group consisting of organic solvents, ionic liquids, silicone oils, organic oils, fluorinated liquids, and liquid metals.

3. The method of claim 1 wherein the common solvent is an aqueous solvent.

4. The method of claim 1, wherein the common solvent is an organic solvent.

5. The method of claim 1, wherein the phase components are selected to be biologically compatible.

6. The method of claim 1, wherein the biological sample comprises cells.

7. The method of claim 6, wherein the cells are selected from the group consisting of animal, plant, protozoan, and prokaryotic cells.

8. The method of claim 6, wherein one or more phases comprises a lysing agent to cause the cells to lyse, the biological analyte of interest being recovered from cell lysate.

9. The method of claim 1, wherein the biological analyte is selected from the group consisting of organelles, cell fragments, cell membranes, cell membrane fragments, viruses, virus-like particles, bacteriophage, cytosolic proteins, secreted proteins, signaling molecules, embedded proteins, nucleic acid/protein complexes, organelles, minicells, nucleic acid precipitants, chromosomes, nuclei, mitochondria, chloroplasts, flagella, biominerals, protein complexes, and protein aggregates.

10. The method of claim 1, wherein the biological sample comprises one or more parasites selected from the group consisting of worms, insects, protozoa, arachnids, and arthropods.

11. The method of claim 1, wherein the biological sample comprises a biological fluid.

12. The method of claim 1, wherein the biological sample is selected from the group consisting of food, juice, and milk.

13. The method of claim 12, wherein the biological sample is tested for contaminants selected from the group consisting of pathogens, pests, heavy metals, and pesticides.

14. The method of claim 1, wherein the biological sample comprises one or biological carriers selected from the group consisting of whole blood, plasma, serum, sweat, feces, urine, saliva, tears, vaginal fluid, prostatic fluid, gingival fluid, amniotic fluid, intraocular fluid, cerebrospinal fluid, seminal fluid, sputum, ascites fluid, pus, nasopharengal fluid, wound exudate fluid, aqueous humour, vitreous humour, bile, cerumen, endolymph, perilymph, gastric juice, mucus, peritoneal fluid, pleural fluid, sebum, vomit, and combinations thereof.

15. The method of claim 1, wherein the biological analyte is separated and analyzed to distinguish cell states selected from the group consisting of normal cells, diseased cells, parasitized cells, cancer cells, foreign cells, and infected cells.

16. The method of claim 1, wherein the sample comprises a plurality of analytes and each analyte migrates to a different location in the phase-separated system.

17. The method of claim 1, wherein after migration, the analyte resides at a boundary location.

18. The method of claim 1, wherein the boundary location is at an interface between a phase with a density greater than the density of the analyte and a phase with a density that is less than the density of the analyte.

19. The method of claim 1, wherein after migration, the analyte resides within a phase of the phase-separated system whose density matches the density of the analyte.

20. The method of claim 1, wherein the analyte/phase-separated system is centrifuged to accelerate migration of the analyte.

21. The method of claim 1, wherein the analyte migrates under gravitational forces.

22. The method of claim 1, wherein the analyte migrates under buoyancy forces.

23. The method of claim 1, wherein the phase separated system is supported in a column or test tube.

24. The method of claim 1, wherein the phase separated system is supported in a capillary tube, plastic test tube, falcon tube, culture tube, well plates, cuvette, along a filament, or on a sheet.

25. The method of claim 1, wherein the surfactant is selected from the group consisting of polysorbate, CHAPS, polyoxyethylene-polyoxypropylene, 1-O-Octyl-β-D-glucopyranoside, 4-(1,1,3,3-Tetramethylbutyl)phenyl-polyethylene glycol, 2-(Perfluoroalkyl)ethyl methacrylate, N,N-dimethyldodecylamine N-oxide, polyethylene glycol dodecyl ether, sodium dodecyl sulfate, sodium cholate, nonylphenol polyoxyethylene, benzylalkonium chloride, and dodecyltrimethylammonium chloride.

26. The method of claim 1, wherein the polymer is selected from the group consisting of dextran, polysucrose, poly(vinyl alcohol), poly(2-ethyl-2-oxazoline), poly(methacrylic acid), poly(ethylene glycol), polyacrylamide, polyethyleneimine, hydroxyethyl cellulose, polyvinylpyrrolidone, carboxy-polyacrylamide, poly(acrylic acid), poly(2-acrylamido-2-methyl-1-propanesulfonic acid), poly(diallyldimethyl ammonium chloride), poly(styrene sulfonic acid), polyallylamine, alginic acid, dextran sulfate, chondroitin sulfate A, diethylaminoethyl-dextran, poly(2-vinylpyridine-N-oxide), polydimethylsiloxane, and poly(propylene glycol).

27. The method of claim 1, wherein the polymer or surfactant is selected from the group consisting CHAPS, polyoxyethylene-polyoxypropylene, dextran, polysucrose, poly(vinyl alcohol), poly(2-ethyl-2-oxazoline), poly(ethylene glycol), polyacrylamide, hydroxyethyl cellulose, polyvinylpyrrolidone, carboxy-polyacrylamide, dextran sulfate, and poly(2-vinylpyridine-N-oxide).

28. The method of claim 1, wherein the polymer is selected from the group of GRAS polymers.

29. The method of claim 1, wherein the polymer is selected from the group of homopolymers, random copolymers, block copolymers, graft copolymers, ter-polymers, dendrimers, star polymers and combinations thereof.

30. The method of claim 29, wherein the polymer is linear, branched and/or cross-linked.

31. The method of claim 1, further comprising one or more additives selected from the group consisting of miscible surfactants, salts, dyes, nutrients, vitamins, antibiotics, anticoagulants, and buffers.

* * * * *